United States Patent [19]

Gravatt

[11] Patent Number: 4,552,570

[45] Date of Patent: Nov. 12, 1985

[54] ADSORBENT FRACTIONATOR WITH AUTOMATIC CYCLE CONTROL AND PROCESS

[75] Inventor: Barton A. Gravatt, Homer, N.Y.

[73] Assignee: Pall Corporation, East Hills, N.Y.

[21] Appl. No.: 577,728

[22] Filed: Feb. 8, 1984

Related U.S. Application Data

[63] Continuation of Ser. No. 351,677, Feb. 23, 1982, abandoned, which is a continuation of Ser. No. 267,964, May 27, 1981, abandoned, and Ser. No. 145,938, May 2, 1980, abandoned.

[51] Int. Cl.$^4$ ............................................ B01D 53/04
[52] U.S. Cl. ............................................ 55/20; 55/33; 55/58; 55/74; 55/163; 55/179; 55/387
[58] Field of Search ................ 55/20, 33, 58, 62, 74, 55/75, 161–163, 179, 180, 208, 387, 389; 361/286, 313, 328–330

[56] References Cited

U.S. PATENT DOCUMENTS

| | | | |
|---|---|---|---|
| 1,882,316 | 10/1932 | Cleary | 361/286 X |
| 2,703,628 | 3/1955 | Pompeo et al. | 55/161 |
| 2,800,197 | 7/1957 | Wynkoop | 55/58 |
| 2,944,627 | 7/1960 | Skarstrom | 55/58 X |
| 3,012,176 | 12/1961 | Williams et al. | 361/313 |
| 3,448,561 | 6/1969 | Seibert et al. | 55/20 |
| 3,513,631 | 5/1970 | Seibert et al. | 55/33 |
| 3,538,403 | 11/1970 | Carollo | 361/330 X |
| 3,659,399 | 5/1972 | Kauer, Jr. et al. | 55/33 |
| 3,802,268 | 4/1974 | Thoma | 361/286 |
| 4,127,395 | 11/1978 | McKey et al. | 55/20 |
| 4,197,095 | 4/1988 | White, Jr. et al. | 55/20 |

FOREIGN PATENT DOCUMENTS 633137 12/1949 United Kingdom .
677150 8/1952 United Kingdom .

*Primary Examiner*—Robert Spitzer
*Attorney, Agent, or Firm*—Leydig, Voit & Mayer, Ltd.

[57] ABSTRACT

A method and apparatus are provided for adsorbing water vapor from a mixture thereof with a second gas to reduce the water vapor concentration in the mixture to below a permissible maximum concentration. The advance of the moisture front in a sorbent bed during either adsorption or regeneration or both is detected by determining the change in the moisture content of the sorbent as a function of the capacitance of a capacitor in which the sorbent is the dielectric. During adsorption, capacitance must be observed by way of a capacitor at least at a point in the bed sufficiently far from the end of the bed to prevent effluent having a limiting maximum moisture content from leaving the bed. When the capacitance at that point has reached a predetermined value corresponding to a selected moisture content on the sorbent, the adsorption or regeneration cycle is discontinued.

13 Claims, 8 Drawing Figures

ADSORBENT FRACTIONATOR WITH AUTOMATIC CYCLE CONTROL AND PROCESS

This application is a continuation of application Ser. No. 351,677, filed, Feb. 23, 1982, now abandoned and in turn a continuation of application Ser. No. 267,964 filed May 27, 1981, now abandoned, and application Ser. No. 145,938 filed May 2, 1980 now abandoned.

Desiccant dryers have been marketed for many years and are in wide use throughout the world. The usual type is made up of two desiccant beds, one of which is being regenerated while the other is on the drying cycle. The gas to be dried is passed through the one desiccant bed in one direction in the drying cycle, and then, at a predetermined time interval, when the desiccant can be expected to have adsorbed so much moisture that there is a danger than the required low moisture level of the effluent gas will not be maintained, the influent gas is switched to the other bed, and the spent bed is regenerated by heating and/or by evacuation and/or by passing dry purge gas therethrough usually in counterflow.

Desiccant dryers on the market today are of two general types, a heat-reactivatable type, in which heat is applied to regenerate the spent desiccant at the conclusion of the drying cycle, and a heaterless dryer, in which heat is not applied to regenerate the spent desiccant at the conclusion of the drying cycle, but which relies upon the use of a purge flow of dry gas, usually effluent gas from the bed on the drying cycle, which is passed through the spent bed at a lower pressure, with rapid cycling to conserve the heat of adsorption to aid in the regeneration of the spent bed. The use of a parge gas to regenerate at a lower pressure than the line pressure of the gas being dried is not, however, confined to heaterless dryers, but was used in heat-reactivated desiccant dryers for many years before the advent of the heaterless type.

Both types of dryers are operated with fixed time drying and regenerating cycles, usually equal in duration, with the length of the cycles being fixed according to the volume of desiccant available and the moisture content of the influent air. The time of the cycle is invariably fixed at much less time than might be permitted, in order to ensure that the moisture content of the effluent gas will always meet the system requirements. As the drying cycle proceeds, the desiccant bed becomes progressively more and more saturated from the inlet end towards the outlet end, and less and less capable of adsorbing moisture that is carried through it by the influent gas. Removal of moisture from the influent gas depends upon the rate of flow of the gas and the rate of moisture adsorption and moisture content of the adsorbent, as well as the temperature and pressure of gas within the bed. The rate of adsorption by the desiccant may decrease as the desiccant becomes loaded. Since the moisture content of an influent gas is rarely constant, the demand put upon the desiccant bed can vary, sometimes rather rapidly, and sometimes within rather wide limits. Consequently, a fixed time drying cycle must always be short enough to give a safe margin for moisture removal at maximum moisture content of the influent gas, and this means that frequently a fixed time cycle must be rather short, to be sure it is ended before the available remaining moisture capacity of the bed reaches too low a level. This means, of course, that in the average cycle, the moisture capacity of the bed may not be well utilized.

The life of a desiccant that is heated in order to regenerate it is to a considerable extent dependent upon the frequency of regeneration. It is a rule of thumb in the trade that a desiccant bed is good for a certain number of regenerations, and no more. Obviously, then, the effective life of a bed is shortened unnecessarily, whenever during each drying cycle the moisture capacity is not effectively utilized. Furthermore, the inability to achieve a full utilization of the effective bed capacity during each drying cycle, both in the case of heat-reactivated and heaterless dryers, means that the volume of the desiccant bed must be more than what might be required, to provide the reverse capacity needed to adsorb extreme but occasional moisture levels of the influent gas during the fixed time period of the drying cycle.

Inefficient utilization of moisture capacity also leads to a considerable waste of purge gas with each cycle. Purge gas is normally bled off from the effluent gas, for the purpose of regeneration of a spent bed, and correspondingly reduces the yield of effluent. Each time a bed is transferred from the drying cycle to the regenerating cycle, a volume of purge gas equal to the open volume of the bed vessel is necessarily dumped, and lost. Short cycling means higher purge losses than long cycling.

Such losses are particularly severe in the case of heaterless dryers, which require much more frequent cycling. Indeed, the choice between a heat-regenerated and a heaterless dryer frequently is dictated by the frequency of recycling required. Skarstrom in U.S. Pat. No. 2,944,627, dated July 12, 1969, describes a type of heaterless dryer which parports to represent an improvement on those described some years earlier by Wynkoop, U.S. Pat. No. 2,800,197, dated July 23, 1957, and the British Pat. Nos. 633,137 and 677,150. Skarstrom showed that by very rapid cycling between adsorption and desorption in the respective zones, the desorption cycle could effectively utilize the heat of adsorption for regeneration of spent desiccant. Skarstrom accordingly taught the use of times in the adsorption cycle and exceeding two to three minutes, preferably less than one minute, and very desirably less than twenty seconds. Such cycling times are of course shorter than Wynkoop's which was of the order of thirty minutes or higher, or the cycling times ranging from five minutes to thirty minutes, of British Pat. No. 633,137. British Pat. No. 677,150 demonstrated that the adsorption and desorption cycles need not necessarily be equal.

The drawback of the Skarstrom system, however, is the very considerable volume of purge gas lost with each cycle, and this loss is very much greater at a cycling time of, for instance, ten seconds, as compared to the British patents' five to thirty minutes, and Wynkoop's thirty minutes or longer. In the short Skarstrom cycles, of course, the capacity of the desiccant bed is very little utilized, but when no heat is applied to effect regeneration of the desiccant, it becomes more important not to carry the moisture content of the adsorbent beyond a certain minimum on the adsorption cycle, or it will be impossible to effectively regenerate the adsorbent on the regeneration cycle.

Dryers have been provided with moisture detectors in the effluent line, to measure dewpoints in the effluent gas. Because of their slow response to relative insensitivity to low dewpoints, however, such devices have not been and cannot be used to determine the cycling of a dryer when an effluent of low dewpoint or relative humidity is desired, since by the time the detector has sensed moisture in the effluent the front has broken through the bed.

U.S. Pat. No. 3,448,561, patented June 10, 1969 to Seibert and Verrando, provides a process and apparatus for drying gases which make it possible to effectively utilize the moisture capacity of a desiccant bed, by providing for regeneration thereof only when the moisture load on the bed requires it, and thus obtain optimum efficiency in use. During each adsorption cycle, the sorbent can be brought to the limiting moisture capacity at which regeneration can be effected under the available regenerating conditions, whether these be with or without the application of heat, and with or without the application of reduced pressure. This is made possible in accordance with the invention by detecting the advance of the moisture front within the bed, as evidenced by the moisture content of the gas being dried, and halting the drying cycle whenever the front has reached a predetermined point in the bed, short of breaking out of the bed. This can be done automatically by providing in the desiccant bed means for sensing the moisture content of the gas being dried, and means responsive to moisture content to halt the drying cycle whenever a predetermined moisture content in the gas being dried is reached at that point.

The advance of the moisture front in a bed of desiccant as it gradually adsorbs moisture is a well known phenomenon in the desiccant drying art, and is discussed in numerous patents, for example Skarstrom U.S. Pat. No. 2,944,627. During the greater part of the drying cycle, the sorbent efficiently sorbs moisture from gas passing over it. When the sorbent capacity of the desiccant approaches zero, however, the moisture content of gas passed over it rises, sometimes rather sharply. If moisture content, dewpoint or relative humidity of the gas be measured, and plotted against time, any rise in moisture content is noted, and if this rise be sudden, it can even be observed as a change in slope. In any case, the increasing moisture content of the effluent exceeds a predetermined minimum, and can rapidly approach the moisture content of the influent gas. The portion of this curve at the point where it exceeds the selected minimum moisture content in effect represents the moisture front, which can in the case of a change in slope assumes an S-shape or some other shape, and if this be observed in terms of the length of the bed, it will be found to progress from the influent end to the effluent end of the bed as the adsorption cycle proceeds. The objective is to conclude the cycle before the moisture front or change in slope of the curve reaches the end of the bed, since thereafter the rise is so rapid that delivery of undesirably moist effluent can hardly be prevented.

In accordance with the invention of U.S. Pat. No. 3,448,561, this is prevented by detecting the advance of the front at a point in the bed sufficiently spaced from the effluent end to permit terminating the drying cycle before the front reaches the effluent end.

In accordance with the present invention, a process is provided for reducing the concentration of water vapor in a mixture thereof with a second gas to below a limiting maximum concentration thereof in the second gas, which comprises passing the mixture in contact with from one end to another end of a bed of a sorbent having a preferential affinity for the water vapor; adsorbing water vapor thereon to form a gaseous effluent having a concentration thereof below the maximum, and forming a concentration gradient of water vapor in the bed progressively decreasing from one end to the other end as the adsorption continues and an increasing concentration of water vapor in the second gas defining a concentration front progressively advancing in the bed from the one end to the other end as sorbent capacity therefor decreases; detecting the advance of the moisture front in the bed by determining the change in the moisture content of the sorbent as a function of the capacitance of a capacitor in which the sorbent is the dielectric at least at a point in the bed sufficiently far from the end of the bed to prevent effluent having a limiting maximum moisture content from leaving the bed; and then discontinuing passing the gaseous mixture in contact with the bed before such effluent can leave the bed and the limiting maximum concentration of water vapor in the second gas can be exceeded.

The invention also provides apparatus for reducing the concentration of water vapor in a mixture thereof with a second gas to below a limiting maximum concentration thereof in the second gas, comprising, in combination, a vessel; a chamber therein for a bed of sorbent having a preferential affinity for the water vapor; a line for delivering influent gas at an inlet end of said bed; a line for delivering effluent gas from an outlet end of said bed; a capacitor having two conductors of selected surface area spaced from each other a sufficient distance to define a space sized to accommodate a volume of sorbent as the dielectric whose change in moisture content, detected for example as a function of dielectric constant, causes a change in capacitance thereof; means responsive to the change in capacitance to give a signal when a selected capacitance indicating a selected moisture content is reached or exceeded; and means for closing off the influent flow of gas in response to the signal.

Thus, in the process of the invention, the concentration of a first gas in a mixture thereof with a second gas is reduced to below a limiting maximum concentration thereof in the second gas, by passing the mixture in contact with and from one end to another end of bed of a sorbent having a preferential affinity for the first gas; adsorbing first gas thereon to form a gaseous effluent having a concentration gradient of first gas in the bed progressively decreasing from one end to the other end as the adsorption continues, and an increasing concentration of first gas in the second gas defining a concentration gradient progressively advancing in the bed from the one end to the other end as sorbent capacity therefor decreases; detecting the advance of the gradient in the bed as a function of the change of moisture content of the bed and thereby of the capacitance of capacitor in which the sorbent is the dielectric; and then discontinuing passing the gaseous mixture in contact with the bed before effluent having a limiting maximum first gas content can leave the bed.

This invention is applicable to gas adsorption fractionating systems wherein any part or the entire sorbent bed is heated to effect regeneration; to systems wherein no heat is applied to effect regeneration; to systems wherein regeneration is effected at reduced pressure; and to systems utilizing a purge gas flow; and to systems combining one or more of these features.

As a further feature in accordance with the invention, since the regeneration cycle need not be and in most cases is not of a duration equal to the drying cycle, the sorbent bed being regenerated can be closed off, and heating, purge, evacuation, or whatever regeneration system is used discontinued when regeneration is complete. The remainder of the cycle time can be used, for instance, for cooling down of the regenerated bed, so that it is at a convenient and efficient temperature for adsorption when the flow of influent gas to that bed is resumed.

The drying apparatus in accordance with the invention comprises as the essential components a sorbent bed adapted for periodic and preferably counterflow regeneration and one or a plurality of capacitors in the bed for detecting the moisture content therein at a point in the bed sufficiently distant from the effluent end thereof to enable termination of a cycle before effluent exceeding a limiting maximum concentration of gas being adsorbed can leave the bed.

If in addition or in the alternative it is the regeneration of the bed that is to be observed as a function of capacitance, then the capacitor or capacitors are placed at a point in the bed to enable termination of the regeneration when desorption of adsorbed gas has reached a selected low level or is complete.

Optionally, the apparatus includes means for applying heat during such regeneration. Such means can extend throughout the bed, or it can be limited to only that portion of the sorbent bed having a high moisture content, of the order of 20% of its moisture capacity or higher, at the conclusion of a drying cycle, i.e., to only that portion first contacted by influent flow during a drying or adsorption cycle. In this case the remainder of the sorbent bed is not heated during regeneration, and consequently no heating means are provided therein. The unheated proportion of the bed volume can accordingly be as large as desired. Usually from one-fourth to three-fourths of the bed volume, preferably from one-third to two-thirds of the volume, will be heated.

In effect, the unheated portion of such a bed constitutes a reserve bed, which in the normal drying cycle may not be required at all, and in which in any case the sorbent is apt to adsorb only a relatively small proportion, less than 20%, of its capacity of moisture, but which is present in order to prevent the delivery of effluent gas of undesirably high moisture content in the unlikely event that moisture is not sufficiently adsorbed in the portion of the bed provided with heating means. The moisture-adsorbing capacity of the reverse portion of the bed is so little used that the reserve sorbent is regenerated by the purge flow, whether or not the purge flow is heated, and any moisture carried forward from this portion by purge flow therethrough is of course effectively removed from the bed after passage through the heated portion thereof.

While the apparatus of the invention can be composed of one desiccant bed, the preferred apparatus employs a pair of desiccant beds, disposed in appropriate vessels, which are connected to the lines for reception of influent gas to be dried, and delivery of effluent dried gas.

The drying apparatus can also include a check valve or throttling valve for the purpose of reducing pressure during regeneration, and multiple channel valves for cycling the flow of influent gas between the beds and for receiving the flow of effluent gas therefrom. In addition, a metering or throttling valve can be included to divert a portion of the dried effluent gas as purge in counterflow through the bed being regenerated.

The capacitor can sense moisture content as a function of capacitance at any portion in the desiccant bed. In some dryers, such as heaterless dryers, which operate at very low total moisture levels on a desiccant bed per drying cycle, it may be desirable to place the capacitor very close to the inlet, say, from one-fiftieth of the length of the bed from the inlet to half way down the bed. Usually, for optimum results, at flow rates of up to 150 ft/min., to ensure that a breakthrough of effluent of undesirably high moisture content is prevented, the capacitor is placed at a point within the range from two-thirds to one-fiftieth of the length of the bed from the effluent or outlet end. If the capacitor is sufficiently quick in response, however, or the permissible moisture content of the effluent sufficiently high, it can be placed adjacent to the outlet port from the bed.

To some extent, the position of the capacitor in the bed is determined by the rate of flow of effluent gas through the bed, allowing the capacitor time to react to the moisture content therein before the effluent exceeding the limiting maximum moisture content can break through the bed. In general, the higher the rate of flow, the further the capacitor should be placed from the effluent end of the bed, so as to ensure that the effluent exceeding the limiting maximum moisture content is detected soon enough to prevent its leaving the bed and entering the system being conditioned.

The type of capacitor and its position in the bed will be selected to detect a moisture level in the gas being dried in time to give a signal before effluent exceeding the limiting maximum moisture content can leave the bed. The margin of safety required for a particular system is easily determined empirically, obtaining data and plotting moisture content curves for the particular system to be used. This one skilled in the art can do without the exercise of invention.

Any capacitor of conventional design can be used. In the simplest form a pair of flat metal sheets parallel to one another are spaced apart at a variable or fixed distance. There or more flat parallel metal sheets can be used by connecting alternate sheets togehter to form a stack of interleaved sheets. Several pairs of sheets can be mounted at one level in a sorbent bed and the pairs connected in parallel electrically.

A cylindrical form has a tubular conductor with a wire, rod or tubular conductor mounted inside it, concentrically or eccentrically. An electrically conducting housing, tank or shell receiving the sorbent bed could serve as one conductor and the other conductor could be a heater tube or other fixture embedded in the desiccant.

The conductor used for a plate can be of any form: wire, rod, sheet, strip, mesh, sintered metal, etc., as long as it is electrically conductive. It is not necessary that sheet conductors be parallel or that tubular conductors be concentric, provided they be electrically isolated from one another. The conductors can be fixed or adjustable, to allow adjustment of the capacitor.

The spacing between the two conductors of the capacitor is determined by the volume required to accommodate in the space a uniform packing of desiccant. The spacing should be as close as possible since the sensitivity of the capacitor decreases as the spacing increases. The conductors can be bare metal or coated with an electrically insulating layer to isolate them from the desiccant, if the desiccant exhibits undesirably high conductivity. Such an insulating layer can include non-electrically conducting plastics such as polyolefins, polyethylene, polypropylene, and polyisobutylene, synthetic and natural rubbers, epoxy resins, ceramics, and glass. Since the volume of sorbent between the two conductors of the capacitor is used as a typical sample showing the condition of the sorbent bed, it is important that it receive all or a uniform portion of the gas flow through the bed. To this end, the conductors should be more or less in-line with the flow, and not in a cul-de-sac at one side of the flow.

If the entire shell of a vessel containing the sorbent bed functions as one plate of the capacitor, and a concentric rod, wire, tube or cylinder extending for part of all of the interior length of the shell as the other, the capacitor senses the total amount of water adsorbed by the desiccant bed, rather than a sample representation of the moisture head at a particular location in the bed.

Signal conditioning to convert the change in capacitance of a capacitor into an electrical, mechanical, audible, or visual signal can be accomplished in any of several ways. LM2917N integrated circuits made by National Semiconductor are intended for use as frequency-to-voltage converters, but with suitable external components and connections can be made to function as capacitance-to-voltage converters. A bridge circuit excited by a sine wave can also be used to generate a voltage proportional to capacitance. The sine wave can be generated by a circuit built with operational amplifiers, for example, National Semiconductor part No. LM741N. The probe could be used as the capacitor in a series of parallel capacitor-inductor circuit excited by a constant frequency, constant amplitude sine wave. By proper selection of the exciting frequency and the value of the inductor, such a circuit can be designed to resonate at any value of capacitance over the range sensed by the capacitor. The output of such a circuit changes markedly when the capacitance reaches the value necessary to cause resonance. Again, the exciting sine wave could be generated using LM741N or similar operational amplifiers. The capacitor can also be used as a feedback component in an operational amplifier configured as an inverting or non-inverting amplifier and used to amplify a constant frequency, constant amplitude sine wave. Such a circuit would have a sine wave output with its amplitude modulated by variations in capacitance.

One or more capacitors can be installed in at least one and preferably all of the sorbent beds of the gas fractionating system.

Two or more capacitors at selected locations in a sorbent bed can detect the progress of a moisture gradient or sorbed component gradient through the bed. A capacitor can be mounted in a portion of a bed which normally adsorbs very little or no detectable water vapor or other sorbed component and used to trigger an alarm if water or other sorbed component appears in that area of bed. Two capacitors at different levels in the bed could be used to compare the capacitance with a "reference" capacitor located in a portion of the bed which is either always wet or always dry, with the "sensing" capacitor located in a portion of the bed which cycles from dry to wet and back during normal operation.

A capacitor can be used to give an indication of the condition (i.e. water-absorbing capacity) of the desiccant in a dryer, by monitoring the loss of water adsorbing capacity in the desiccant as reflected in a gradual decrease in the maximum capacitance, by mounting it in a portion of the bed which is saturated with adsorbed water at some stage in the operating cycle.

The capacitor for determining moisture content of the dessiccant can be located in the sorbent bed, but it need not be, and can be in a representative sample of the sorbent bed, of sufficient volume to give a change in capacitance related to moisture content of the main sorbent bed, and in another location remote from the bed. In the latter event, a portion of the process or parge gas is circulated through it, causing a proportional change in moisture content of the sample sorbent bed in terms of dielectric constant, for example. Such a capacitor will detect a condition of the sorbent in the sample bed that is related to that of the main sorbent bed onstream, and by appropriate calibration can signal a response before the moisture front of effluent gas can break out of the bed.

The following exemplify preferred locations for capacitors in the sorbent beds for control of adsorption and/or regeneration cycle time in heated dryers and in heaterless dryers.

In heated dryers each bed should have one capacitor mounted at the point in the bed reached by the moisture front when the bed has been exhausted. The relatively large change in capacitance caused by the change in absorbed water content of the desiccant between the capacitor conductors as the moisture front traverses the capacitor is converted into a signal to initiate cycling of the bed from onstream to offstream, for regeneration. If there are two beds, the regenerated bed can be put onstream at the same time. The criterion for bed exhaustion is the arrival of the moisture front at a point in the bed preselected to maintain a given effluent dew point.

After capacitor in the bed of a heated dryer can be used to sense completion of regeneration when the bed is offstream for regeneration.

Since the method of optimizing cycling in heaterless dryers is dictated by the fixed cycle time required in such dryers, the capacitor is best used to control the duration of delivery of purge gas to the regenerating bed. The most direct, and preferred, approach is to mount the capacitor near the influent end of each bed to detect the arrival of the moisture front at that end of the bed as it is driven towards that end by the purge gas during regeneration. Upon arrival of the moisture front at that point which ensures maintenance of effluent dew point under maximum moisture load conditions when that bed is switched back on stream, the purge gas would be shut off. Another more complex and less desirable arrangement places the capacitor at a point in the bed through which the moisture front would pass during operation under typical conditions. The time of which the moisture front passed the capacitor during the drying cycle for that bed would be stored, and would be correlated with the rate at which moisture was being adsorbed onto the desiccant in that bed. That time would be used to calculate, such as via a microprocessor, the amount of purge required for regeneration of that bed when it entered the regeneration portion of the NEMA cycle.

The fundamental advantage of the capacitor is that it gives, relative to other sensing and/or computing methods of monitoring dryer performance, a direct indication of the moisture content of the bed, and therefore of the amount of bed capacity which is being used for adsorption, which is correlated to the depth in the bed to which the moisture front has penetrated, and hence, the extent to which the bed has been exhausted. There is a direct correlation between this information and the actual parameter of interest, i.e. the dew point of the effluent process gas, whether the capacitor is used to determine the position of the moisture front during drying or during regeneration. The sensing and control circuitry is designed to give quantitative measurements of desiccant loading, dew point and other parameters by relying on the quantitative change in moisture content sensed as dielectric content. The response of a capacitor to changes in the amount of water adsorbed onto desiccant between its plates is instantaneous.

The means responding to the change in capacitance in the capacitor with moisture content can be electrical or mechanical or chemical or any combination thereof, but it is preferably arranged, responsive to a preselected change in capacitance, or to a preselected capacitance, to signal or control suitable valving, so as to conclude the drying cycle or regeneration cycle, and switch the influent and effluent gases from one tank to the other, at the time the predetermined maximum moisture level in the effluent gas is reached.

The time required for the moisture content in the effluent gas to reach the predetermined level is directly correlated with the moisture capacity and moisture content of the sorbent. As the gas proceeds across the length of a desiccant bed, its moisture content is progressively diminishes, according to the rate of adsorption of moisture of the desiccant. Since the rate of adsorption of moisture by the desiccant is dependent upon the moisture capacity, the gas pressure, the temperature and the rate of flow of gas, it will be apparent that for a given temperature and pressure of influent gas, the predetermined moisture level of the effluent gas will be reached only when the moisture load of the sorbent has also reached a predetermined level. Since the capacitor responds directly to moisture load on the sorbent, it is possible in accordance with the invention to adjust the drying cycle length precisely in accordance with the moisture content or load of the sorbent, and thus effectively utilize the moisture capacity thereof in each drying cycle, without however introducing a danger of breakthrough.

Consequently, the desiccant dryers in accordance with the invention can be arranged to operate to a predetermined moisture load on the desiccant during each drying cycle. This means that if the moisture level of the influent gas varies, the drying cycle length is also automatically adjusted accordingly. The result is that a drying cycle is not terminated until it is necessary to do so, and unnecessary to regenerations of the desiccant are eliminated. It thus also becomes unnecessary to build in a reserve capacity of desiccant; since the drying cycle depends on the moisture capacity of the desiccant volume utilized, a smaller volume of desiccant than was formerly required will now be sufficient. At the same time, the volume of purge lost during each cycle is kept to an absolute minimum. In effect, the desiccant dryers of the invention can be made to automatically time their drying cycles according to the demand made upon them by the moisture content of the influent gas, and consequently such dryers in accordance with the invention are referred to as demand cycle dryers.

The regenerating cycle, on the other hand, need not be and preferably is not automatically the same in length of time as the drying cycle. Since the drying cycle can be very greatly lengthened, according to demand, the regenerating cycle can be time-controlled, to end when regeneration is complete, even if the drying cycle continues. This also will ensure that the purge flow and energy used in any heating of the bed will not be wasted when no longer needed. The regeneration cycle can be linked to another capacitor, to end when the sorbent drying ends, if this be before the timed regeneration cycle is completed, or the capacitor can be linked to the regeneration cycle capacitor or timer, to be ineffective to end the drying cycle until regeneration be complete. The same capacitor can also be used to control the regeneration cycle, as indicated above.

In order to prevent unnecessary dumping to the process gas in the sorbent bed in heaterless dryers, and concomitant loss of process gas when the flow of process gas is very low, and does not warrant any significant flow of purge gas (since the volume of gas lost during dumping would be quite large, compared to the volume of purge gas required for regeneration during conditions of very low process flow, such a mode of operation could effect substantial savings), hysteresis can be introduced into the control mechanism. The capacitance moisture sensor would then terminate regeneration of a sensed capacitance slightly lower than the sensed capacitance required to initiate regeneration. Thus, if a fully regenerated bed were switched onstream under conditions of no process flow, and hence had no downward migration of the mass transfer zone, and no increase in the capacitance of the capacitance probe, it would call for no purge, and no depressurization, when it entered the regeneration half of the cycle. In contrast, a bed without hysteresis would depressurize and purge for a very short period upon entering the regeneration half of the cycle since the capacitance level at which regeneration was terminated would also be interpreted as the (minimum) capacitance level necessary to cause initiation of regeneration.

The degree of hysteresis is determined by optimization of overall efficiency. Large hysteresis saves the maximum amount of process gas which would ordinarily be lost during depressurization, by allowing a substantial amount of water to accumulate in the bed before calling for purge and causing depressurization. At a low flow rate, this means that purge may not be called for for a number of NEMA cycles and as a consequence, the heat of adsorption tends to be lost. On the other hand, relatively small hysteresis makes better use of the heat of adsorption by allowing less water to accumulate in the bed before calling for purge. This means the dryer will call for purge more frequently at a given flow rate, allowing less time for the heat of adsorption to dissipate. The penalty paid is that more process gas is lost via more frequent depressurizations. These two factors mean a trade-off to optimize efficiency, and this trade-off, which may result in a different hysteresis for each size of dryer, is a part of the control circuit design.

The required hysteresis can be introduced into the electronic signal-conditioning circuit shown in FIG. 7. The resistor H is the only component required to introduce the hysteresis. The value of resistor H determines the amount of hysteresis, i.e. the difference between the two capacitance levels at which the output of the circuit goes to a high or a low state.

Hysteresis can also be used by placing two capacitors at slightly different levels in the bed, and using the upper capacitor to signal the end of regeneration and the lower capacitor to signal the need for initiating regeneration in a downflow dryer. In this case, the amount of hysteresis can be adjusted by varying the vertical separation of the two probes.

In accordance with the invention the cycle is concluded before the moisture front or change in slope of the moisture content curve reaches the end of the bed, since thereafter the rise is so rapid that delivery of undesirably moist effluent can hardly be prevented. This is prevented by the capacitor by detecting the advance of the moisture front at a point in the bed sufficiently spaced from the effluent end to permit terminating the drying cycle before the front reaches the effluent end.

The following comparison illustrates the effect of two levels of hysteresis in a capacitance control system on the efficiency of process gas utilization:

|  | High Hysteresis (5.1 Megohm Resistor) | Low Hysteresis (10 Megohm Resistor) |
| --- | --- | --- |
| Run Time | 16.78 hr. | 44.01 hr. |
| Number of NEMA Half Cycles | 201 | 528 |
| Average Porge Duration per Half Cycle | 190 sec. | 170 sec. |

Inlet conditions for the 130DHA used were very nearly identical: 125.8 scfm inlet flow at 67.5 psig for the high test, 124.5 scfm inlet flow at 68 psig for the low test. The low hysteresis test called for purge every cycle. The high hysteresis test saved a total of 66 dumps.

Since the volume of gas lost per dump was equal to about 11 seconds of purge flow at the purge rate used, the high hysteresis run saved process gas equal to 726 seconds of purge flow. Averaged over 201 half cycles, this represented an average savings equivalent to 3.6 seconds of purge flow per half cycle.

This reduces the actual gas consumption per half cycle to the equivalent of 186.4 seconds of purge flow. Thus the high hysteresis test consumed more gas to maintain outlet conditions than the low hysteresis test, even though it saved dumps.

How this is done is best seen in reference to FIG. 1.

FIG. 1 represents a series of curves for the drying of moist gas at 80% relative humidity at temperatures ranging from 100° F. to 70° F., plotting the moisture content of the sorbent bed, determined as a function of the capacitance of the bed, against time for gas being dried, detected by placing capacitors at a series of points X 30 inches in from the effluent end of the bd, and at a series of points Y 24 inches from the effluent end of the bed.

The curves represent a system in which air is at a line pressure of 92 p.s.i.g. and a superficial flow velocity of 65.1 fpm using silica gel (177 lbs) as the desiccant in a bed 60 inches long, and 12⅜ inches in diameter, as in Example 1. The data is typical however of that obtainable using any desiccant under any adsorption conditions.

The principle of the process of the invention is to detect and halt the cycle before the change in slope S of the moisture front has reached the outlet, i.e., in FIG. 1, before about 2.4 hours cycle time for Curve I, about 3.3 hours cycle time for Curve II, about 4.5 hours cycle time for Curve III, about 6.3 hours cycle time for Curve IV. The curves of FIG. 1 show that this can be done by terminating the cycle whenever the moisture level in the sorbent bed at point X and at point Y does not exceed 2%. This moisture content is susceptable of detection by available capacitors.

When capacitors are present at points X and Y in each of the drying cycles represented in FIG. 1, the curves show the moisture content of the sorbent bed when the capacitors are actuated. In all cases, Curves I, II, III and IV, capacitor X is actuated at points, A,C,E and G, and capacitor Y at points B, D,F and H, all before the change in slope $S_2, S_3, S_4$, and thus in time to prevent the moisture front's leaving the bed.

Figure 3:
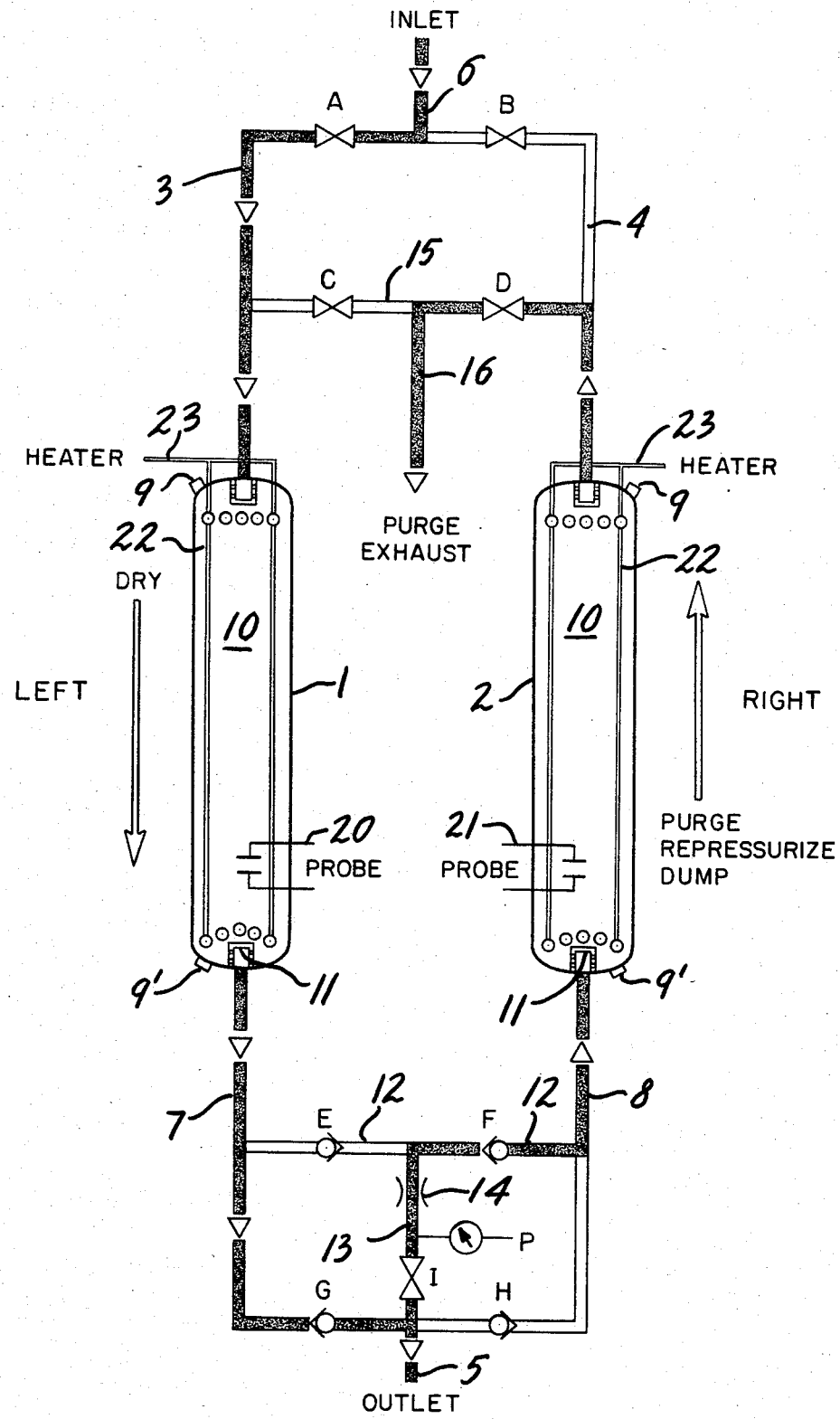
FIG. 3 is a schematic view of a two-bed-heat-reactivatable desiccant dryer in accordance with the invention.

The dryer of FIG. 3 is composed of a pair of desiccant tanks 1 and 2. These tanks are disposed vertically. Each tank contains a bed 10 at desiccant such as silica gel. Also provided in tanks 1, 2 are desiccant fill and drain vents 8, 9 for draining and filling of desiccant in the tanks.

LIes 3, 4 connect the two tanks for introduction of influent gas from line 6 containing moisture to be removed, and lines 7, 8 deliver to outlet line 5 via check valves G, H dry effluent gas freed from moisture after having passed through the dryer. The inlet switching valves A, B, of which only one is open at a time, direct the flow of influent gas to one of the inlet lines 3 and 4, leading the influent gas to the top of each tank.

At the bottom of each tank is a desiccant screen support 11 made of a sintered stainless steel mesh, retaining the desiccant bed 10 in the tanks 1 and 2. Outlet lines 7, 8 from the bottom of tanks 1 and 2, respectively, lead to the outlet line 5.

Line 12 bridges lines 7 and 8, and has check valves E, F for undirectional control of purge flow for regeneration. Line 12 is connected with the outlet line 5 by line 13, via valve I and orifice 14.

Check valves G, H permit only unidirectional flow towards outlet line 5 in lines 7, 8 while check valves E, F, permit unidirectional flow in the opposite direction via orifice 14 and valve I from the outlet line 5 into line 12 and thence in the opposite direction via the other of lines 7, 8 into the bottom of tanks 1, 2 for purge and regeneration of desiccant 10.

Value I is used to control the delivery rate of purge flow to the offstream bed being regenerated. In the line 13 is a purge flow pressure gauge P.

Disposed within each tank at a point above the supports 11 are each of a pair of moisture sensing capacitors 20, 21, for determination of moisture content of the desiccant as a function of the capacitance of a capacitor in which the sorbent is the dielectric.

Bridging lines 3, 4, is line 15 with exhaust valves C, D controlling flow therethrough from the tanks 1, 2 to the exhaust line 16. Only one of valves C, D is open at a time, during regeneration of the sorbent beds 10 in tabs 1, 2.

The capacitors 20, 21 are of the plate type, and are connected to a sensor (not shown) set to respond to a capacitance corresponding to a moisture level to prevent the moisture front from leaving the bed. For instance, if the maximum atmospheric dewpoint that can be tolerated in the effluent gas is −80° C., then the sensor is adjusted to response to a capacitance corresponding to a dewpoint of from −40° F. to 0° F. The sensor shown is of the LM2907N frequency in voltage converter type, but any other type of sensor can be used.

Disposed at the inlet end of each bed 10 and extending approximately the length of the bed is an array of elongated heater elements 22, in this case ten in number. These are evenly spaced through the bed. However, it will be appreciated that a lesser or greater number of elements can be used, according to their heat capacity. The inlet ends of the heaters are provided with electrical connections 23, which extend through the walls of the tanks 1 and 2 and are connected to the electrical system in a manner such that the heaters are turned on when the bed is put on the regenerating cycle, and turned off at the end of a predetermined time, sufficient to effect regeneration of the desiccant, which may be less than the duration of the drying cycle, or which may be equal to the length of the drying cycle, depending upon the time required to activate the capacitors 20, 21.

If tank 1 is on the drying cycle, and tank 2 on the regenerating cycle, with valves A, D open and valve B, C closed, then operation of the dryer is as follows: Wet gas of line pressure, 25 to 350 p.s.i.g., entering through line 6 is diverted by valves A,B into line 3 to tank 1, and passes thence downwardly through the bed 10 past the capacitor 20 to the outlet, whence it is conducted via line 7 through valve G to the outlet line 5. Valves E and H prevent flow in lines 12 and 8, respectively. A portion of the effluent, as controlled by the purge valve I, is then passed through line 13, through orifice 14 where its pressure is reduced to approximately atmopsheric due to open exhaust valve D, into line 12, through check valve F (valve E prevents flow in line 13) to the bottom of the second tank 2, which is on the regeneration cycle, and it passes thence upwardly through the bed 10 to the inlet and thence through the line 15 via valve D, and is vented to the atmosphere through the purge exhaust line 16.

The array of heaters 22 in tank 2 which is being regenerated is activated, and the desiccant bed is baked out while being subjected to the purge flow for the time required to fully regenerate the desiccant. This time may be considerably less than the drying cycle time, which of course is determined not by a fixed time cycle, but by the moisture level in the bed. Consequently, the heaters 22 are timed so as to be activated only for the time necessary to complete regeneration of the desiccant, and when this time has elapsed, they and the timer are automatically shut off. Purge flow of gas is continued only for a time sufficient to cool the desiccant bed to room temperature, at which temperature the adsorption is more efficient, and then it too is automatically shut off by closing purge exhaust valve D, repressurizing the spent bed, readying it for the next cycle. Normally from a half hour to two hours is adequate to effect complete regeneration of a spent bed, if the bed is heated by the heating elements to a temperature within the range from 100° to 250° C. However, other temperatures and times can of course be used, dependent upon the desiccant that is employed.

When the capacitor 20 has sensed the predetermined moisture content on the bed 10 in tank 1, the timer is reenergized, and switches the valves A,B,C, so as to close valve A and open valve B and divert influent gas to line 4 to the top of the second tank 2 on the drying cycle, and open purge exhaust valve C. Purge flow now passes through line 13, orifice 14 and line 12 through valve E to the bottom of the tank 1, which is now on the regeneration cycle. At the time valve A is switched, the heaters 22 in bed 10 are turned on, heating the bed to reactivate the desiccant. This cycle continues until the capacitor 21 senses the predetermined sorbent moisture level in tank 2, whereupon the valves A,B,C,D are again switched, and the cycle is repeated.

Figure 4:
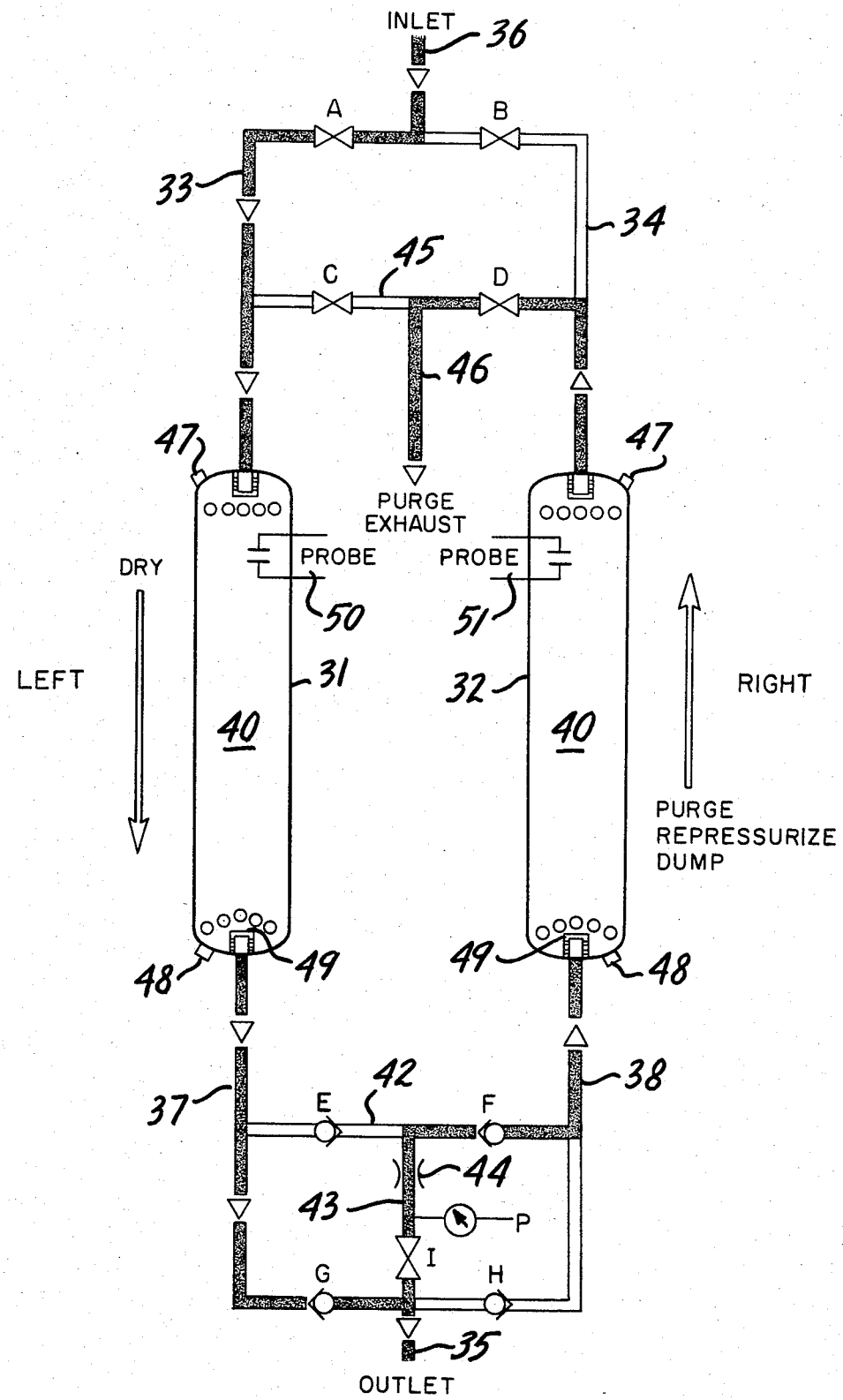
FIG. 4 is a schematic view of a two-bed heaterless desiccant dryer in accordance with the invention.

In the dryer shown in FIG. 4, heat is not employed to effect regeneration of the spent desiccant, and the capacitors 50, 51 are used to detect the advance of the front of desorbed water vapor during desorption.

The dryer is composed of two tanks 31 and 32, fitted with suitable line connections 33,34 for delivering wet gas influent from line 36 via valves A,B, and for delivering dry gas effluent from each tank via lines 37, 38 and check valves G,H to outlet line 35, and with desiccant fill and drain parts 47 and 48, respectively. The desiccant 40 is supported on screen supports 49 in each tank.

The cross line 4, bridges the outlet lines 37, 38 and is fitted with two check valves E,F on either side of a line 43 extending to the outlet line 35. In line 43 is a pressure-reducing orifice 44, beyond which pressure is reduced to approximately atmospheric when purge exhaust valves C or D are open, and purge adjusting valves I for metering flow through the line 43. This controls the volume of purge flow bled off the effluent gas for regeneration of the spent tank, which is read off from the purge flow indicator P.

Another line 45 extends between lines 33 and 34, and is fitted with purge exhaust valves C and D, respectively, which vent purge to the atmosphere, when open, through the exhaust line 46.

At points approximately one-third of the length down the bed in each tank are a pair of capacitors 50, 51, as in FIG. 3, which detect the moisture level in the sorbent bed in terms of capacitance, and respond thereto after regeneration is complete, when a predetermined low moisture level in the bed has been reached, and at that time control the operation of the valves A,B,C,D and repressurization valve I.

If tank 31 is on the drying cycle and tank 32 on the regenerating cycle, with valves A,D open and valves B,C closed, then the operation of the dryer proceeds as follows: Wet gas influent at, for example, 100 p.s.i.g., and a flow rate of 305 s.c.f.m., saturated at 80° F., enters through the inlet 36 into the line 33, passes the valve A and enters the top of the first tank, and thence through the bed of desiccant 40 therein, for example, alumina to the outlet, and thence through filter 49, line 37 (check valve E preventing entry into line 42) and through check valve G to the dry gas outlet line 35. Effluent gas is delivered there at 95 p.s.i.g and 265 s.c.f.m., dewpoint −100° F. Check valve H prevents entry of dry gas into line 38. The remainder of the dry gas effluent, 40 s.c.f.m. in this example, is bled off through the line 43 from the end of line 35 at the outlet and conducted past valve I and orifice 44, where its pressure is reduced to approximately atmospheric, and then through line 42 past check valve F to the bottom of the second tank 32, which is on the regeneration cycle. Purge flow passes through the desiccant bed 40 and emerges into line 34, and thence passes through purge exhaust valve D, whence it is vented to the atmosphere via line 46.

This cycle continues while the moisture front of moisture vapor desorbed from desiccant 40 proceeds upwardly through the bed 32, past capacitor 51. When the moisture front has passed, indicating desorption of water from the bed below the capacitor is complete, a signal is given, and valve D is closed, permitting tank 32 to repressurize, and halting purge flow.

Since the time that each bed can be on the drying cycle before wet effluent can break out of a bed is normally much greater than the length of time required to regenerate the spent bed, inlet valves A,B are timed so as to be actuated after a fixed time interval sufficient to complete regeneration and repressurization of the regenerated desiccant. When this time has elapsed, valves A,B are automatically switched, so as to divert influent gas flow to the regenerated bed.

When the capacitor 51 has detected the predetermined moisture level in tank 32, indicating desorption is complete valve D is closed, allowing bed 32 to repressurize. When the fixed time interval for adsorption on tank 31 has elapsed, the timer closes valve A and opens valve B, so that wet gas influent entering through inlet 36 passes through line 34 to tank 32, while dry gas effluent can now pass from the tank 32 to the dry gas delivery line 35 via line 38. The flow of purge gas in the cross-line 42 is now reversed, and purge flows in line 43 through valve I, and orifice 44, into line 42 and past valve E into line 37 to the tank 31, which is on the regeneration cycle, and thence through the bed 40 to the line 33, and thence through line 45 and valve C to line 46, where it is vented to the atmosphere. This cycle continues until the regeneration of bed 31 is complete, as determined by capacitor 50, whereupon the capacitor closes purge exhaust valve C, to repressurize tank 31. The system continues with tank 32 on the drying cycle until the timer reverses the valves A,B and the cycle is begun again.

Usually, the drying cycle is carried out with gas at a superatmospheric pressure, of the order of 15 to 350 p.s.i.g. The orifice 44 in the cross-line 43 in combination with the purge exhaust valves C and D ensures that the regeneration cycle is carried out at a pressure considerably reduced from that at which the adsorption cycle is effected.

This system includes a fail-safe arrangement to prevent injury in event of bed overhauling and failure to regenerate by providing an overriding timer counting out the time of a predetermined NEMA half-cycle. If the moisture front for desorbed moisture vapor does not reach the capacitor within the maximum time available in the NEMA half-cycle for purging, valve C and D would be closed anyhow, to allow repressurization, and an alarm would be activated. In either case, valve A would be closed and valves B and C opened at the end of the NEMA half-cycle, and valves E,F, G and H would operate to allow the offstream repressurized regenerated bed to come onstream, with a downward flow of influent gas and the onstream beds to depressurize and begin regeneration.

This implementation has the special advantage of minimizing the consumption of purge gas during start up of a heaterless dryer, as maximum purge is called for only as long as required, rather than for a fixed and usually excessive number of cycles.

Another control arrangement for heaterless dryers involves more complex control circuitry. A capacitor in the region of each bed through which the moisture front would pass during the adsorption half-cycle for the bed would be used to determine the time during the adsorption half-cycle at which the front passed the capacitor position. By proper selection of the capacitor position, the time at which the moisture front passes the capacitor position will be a function of how fast the moisture front is moving during the adsorption half-cycle, and hence of the rate at which moisture is being adsorbed. The time at which the moisture front passes the capacitor position can then be stored until the bed enters the regeneration half-cycle. The time can be stored as an electrical voltage or converted to digital information. When the bed enters the regeneration half-cycle, the stored time would then be used to calculate the duration of purge flow necessary to effect regeneration of that bed.

When a dryer with such a control scheme enters the cycle changing stage, the controller would use the elapsed time required for the front to pass stored during the previous half-cycle to determine how long the purge flow should be continued for complete regeneration of that bed. If the purge time required exceeds the maximum purge time available, maximum purge would be delivered and an alarm could be sounded. Under normal operating conditions, the exhaust valve would be closed after regeneration is complete, and the regenerated chamber allowed to repressurize. Meanwhile, the time at which the moisture front moves past the capacitor in the new bed would be stored for subsequent use in calculating the duration of purge flow needed to regenerate that bed when it enters the regeneration half-cycle. At the end of the NEMA half-cycle shown in the schematic, the valves would be operated to direct influent gas flow through the regenerated bed and purge gas through the spent bed, and the regenerated bed would depressurize and begin purging.

This system would also allow minimization of the number of maximum purge cycles required upon start-up of the dryer.

Figure 5:
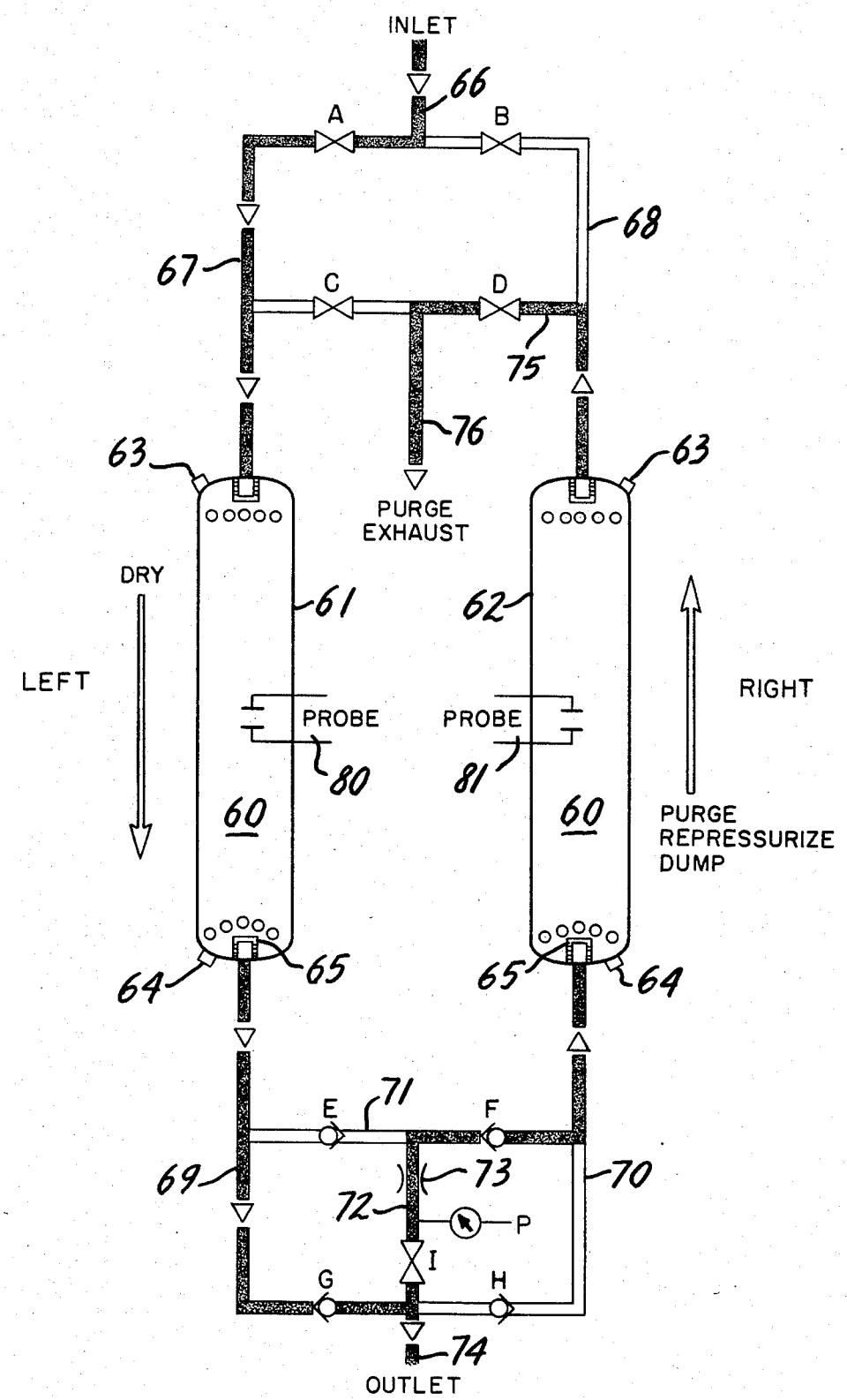
FIG. 5 is a schematic view of another type of two-bed heaterless desiccant dryer in accordance with the invention.

The dryer shown in FIG. 5 uses this arrangement.

The dryer is composed of two tanks 61 and 62, fitted with suitable line connections for delivering wet gas influent and dry gas effluent to and from each tank, and with desiccant fill and drain ports 63 and 64, respectively. The desiccant 60 is supported on screen supports 65 in each tank. Wet gas influent flow from inlet line 66 is controlled by valves A and B, which direct the flow of influent gas either to line 67 or to line 68 and thence to tanks 61,62.

Dry gas effluent leaves the tanks via one of lines 69, or 70 both of which are connected to the dry gas outlet 74. In each line is a check valve G,H. A cross line 71 bridges the outlet lines 69, 70 and is fitted with two check valves E,F, on either side of a parallel line 72 extending to the outlet line 74. In line 72 is a pressure-reducing orifice 73 beyond which pressure is reduced to below approximately atmospheric, when purge exhaust valves C or D are open, and purge adjusting valve I for metering flow through line 72. This controls the volume of purge flow bled off the effluent gas for regeneration of the spent tank which is read off from purge flow indicator P.

The line 75 extends between lines 67 and 68 and is fitted with purge exhaust valves C and D respectively, which control the venting of purge flow to the atmosphere through the line 76.

At points approximately in the middle of each tank are a pair of capacitors 80, 81, which give a signal when a predetermined moisture level in the bed 60 is reached, and control the timer which controls the operation of the valves A, B and also the purge exhaust valves C,D and repressurization valve I.

If the tank 61 is on the drying cycle, and the tank 62 on the regenerating cycle, with valves A and D open, and B and C closed, then the operation of the dryer proceeds as follows: Wet gas influent at, for example 25 p.s.i.g., and a flow rate of 305 s.c.f.m., enters through the inlet 66 into the line 67, passes the valve A and enters the first tank 61 and thence through the bed of desiccant 60 therein, for example, silica gel, past the capacitor 80 to the outlet, and thence through line 69, and check valve G to the dry gas delivery line 74. Effluent is delivered there at 20 p.s.i.g. and 267 s.c.f.m. Check valve H prevents entry of dry gas into line 70. The remainder of the dry gas effluent, 38 s.c.f.m., in this example, is bled off through the line 72 from the outlet and conducted past valve I and orifice 73, where its pressure is reduced to approximately atmospheric, due to the exhaust valve being open, and then through lines 70, 71 via valve F to the second tank 62, which is on the regeneration cycle. Purge flow passes through the desiccant bed 60 and emerges into lines 68, 75 and thence passes through purge exhaust valve D to line 76 where it is vented to the atmosphere.

At the end of a predetermined time, controlled by a timer, purge valve D is closed. Then, when repressurization is complete, the timer switches valves A, B, putting tank 61 onstream and tank 62 on regeneration.

The absorption cycle continues until the capacitor 80 has detected the predetermined moisture level in the sorbent in the tank 62. When a predetermined moisture level in the sorbent bed 60 is detected by capacitor 80, a signal is given and the time required for this level to be reached is stored in an electronic memory device. Meanwhile the tank 61 is being regenerated, and purge flow continues until the time stored by the memory device has elapsed, whereupon exhaust is stopped by closing valve D, allowing bed 61 to repressurize. The timer is reenergized, and when the bed in tank 61 is repressurized, valve I is closed and purge flow cut off. Then, tank 62 continues on adsorption until the fixed time therefor has elapsed, whereupon the timer closes valve A to switch flow from the tank 62 to the tank 61 via line 68, and then opens valve C so that dry gas effluent can now pass to the tank 62 from the dry gas delivery line 66. The flow of purge gas in the cross-line 72 is now reversed and purge flows in line 72 through valve I and line 71 and valve E to the tank 61 which is on the regeneration cycle, and thence through the bed to the line 67, and thence through line 75 through open purge exhaust valve C and line 76, where it is vented to the atmosphere. This cycle continues as before after which the valves are reversed and the cycle begun again.

Usually, the drying cycle is carried out with gas at atmospheric pressure or above, of the order of 15 to 350 p.s.i.g. The orifice 73 in the cross-line 72 and exhaust valves, C, D ensure that the regeneration cycle is carried out at approximately atmospheric pressure, considerably reduced from that at which the adsorption cycle is effected.

To ensure regeneration of the spent bed during the observers time for the regenerating cycle, the time allotted is adjusted, together with the volume of purge flow according to the volume of desiccant, and the pressure at which the desorption is effected. Heaterless dryers operate under equilibrium conditions, and the equilibrium conditions must be maintained under all of the conditions to which the dryer may be subjected in use.

The use of capacitors is of particular application in gas fractionating apparatus utilizing an electronic sequence timer that comprises, in combination, digital integrated circuitry including an oscillator, and a binary counter. The capacitors are in operative connection with the drivers for a plurality of solenoid valves movable between positions permitting and closing off the gas flow through the bed or beds during adsorption and regeneration and control the gas flow through the adsorbent gas fractionator system according to the cycling intervals prescribed in part by the timer and in part by the moisture content of the sorbent bed.

The electronic sequence timer is made up of a combination of conventional and commercially available electronic components, none of which individually forms any part of the invention, but which in combination, in the circuitry to be described, make it possible to prescribe the fixed time intervals required for operation of the gas fractionators.

The heart of the electronic system is an oscillator which generates electric impulses at selected time intervals. The timer is in effect a self-excited electronic circuit whose output voltage is a periodic function of time. The oscillator should be capable of providing a range of time interval delays between pulses, so as to allow selection of the desired time intervals, inasmuch as the short time interval pulses provided by the timer or oscillator are the basic building blocks on which the longer intervals are built up in the binary counter.

In principle, the timer generates pulses at selected time intervals. These are fed to a binary digital counter, which counts these pulses, and is composed of a plurality of stages or bits which in combination store information on the number of pulses at multiples of the time intervals. A plurality of logic gates arranged in a logic module are utilized to interpret the output states of the counter, respond to certain selected output combinations corresponding to the desired time intervals, and operate the solenoid drivers accordingly, thereby achieving the selected time intervals for each of the stages.

One type of timer oscillator utilizes a circuit which makes it possible for it to trigger itself and free-run as a multivibrator. An external capacitor charges through one set of resistors, and discharges through another set. Thus, the timing interval can be varied within a desired range by varying the values of these two sets of resistors, which is readily done by simply selecting resistors of the required resistance. An example of this type of oscillator is the 555. Other types which may be utilized include flip-flop multivibrators, capacitance delayed op-amp with positive feedback, and capacitance-coupled NOR gates.

The binary digital counter receives the pulses from the timing oscillator, and counts them. The counter can include any desired number of units, as required for the timing intervals that need to be determined. In the system shown in the drawing, a 14 stage or bit binary counter is employed, since this is a readily available and quite satisfactory type. In the counter shown in the drawing, each counter stage is a static master-slave flip-flop, and the counter is advanced one count on the negative going transition of each input pulse. Other types can however be used.

This binary counter has a series of stages, each with one input and one output. The output ($0_n$) of each stage is connected to the input of the following stage. The logic output of each stage reverses when its input goes through the transition from logic 1 to logic 0. Thus, a full cycle of any stage requires two cycles of the preceding stage. This results in a frequency reduction of $2^{14}$ (or 16,384:1) in this 14 stage binary counter. This reduction allows a 10 minute cycle to be driven by a 27.3 Hz oscillator. As a general rule, oscillators are more accurate at higher frequencies.

The stages are referred to as $Q_1$–$Q_{14}$. $Q_{13}$ the last (or slowest) stage of this counter, divides the overall cycle into two halves. During the first half, it is at logic 0, and during the second, at logic 1. Similarly, $Q_{13}$ divides the cycle into quarters; $Q_{12}$ into eighths; and $Q_{11}$ into sixteenths. It can be determined which of 16 even divisions or sequences of the cycle the timer is in by monitoring the output of these last four stages. The selected arrangement of AND, NAND, OR and NOR gates interprets these four outputs, and drives the appropriate output transistors, which in turn powers the solenoid valves. The first ten stages of the binary counter (not externally connected) serve as frequency reduction. They could, however, be used to achieve higher resolutions of cycle position if required in more exacting applications.

The logic module includes a number of logic gates, arranged in combinations selected to provide output to power the solenoid drivers during the prescribed time interval for each valve function. Since the function of AND, NAND, OR and NOR gates is well known, and the particular arrangement of these gates will of course depend upon the intervals selected, and the timing oscillator and binary counter devices used, the particular arrangement that can be utilized in a given circuit will be apparent to those skilled in this art. The arrangements shown in the drawings are illustrative of the combinations that can be made.

One minor alteration to the circuitry can give much greater accuracy and repeatabilty when required. This involves the elimination of the oscillator and driving the binary counter with an unfiltered connection to the secondary winding of the power supply transformer. This essentially uses the power line frequency as a substitute for the oscillator. While power line frequency is extremely precise over long periods there is the disadvantage of not being able to adjust this frequency. To some extent, this problem can be alleviated by incorporation of a "divide by n counter". This is an integrated circuit that is wired to give one output pulse for each n input pulses, where n cam be any integer from 3 to 9. The various combinations obtainable by selecting the right n and the right number of binary counter stages after it give a fairly wide selection of cycle duration times.

Figure 6:
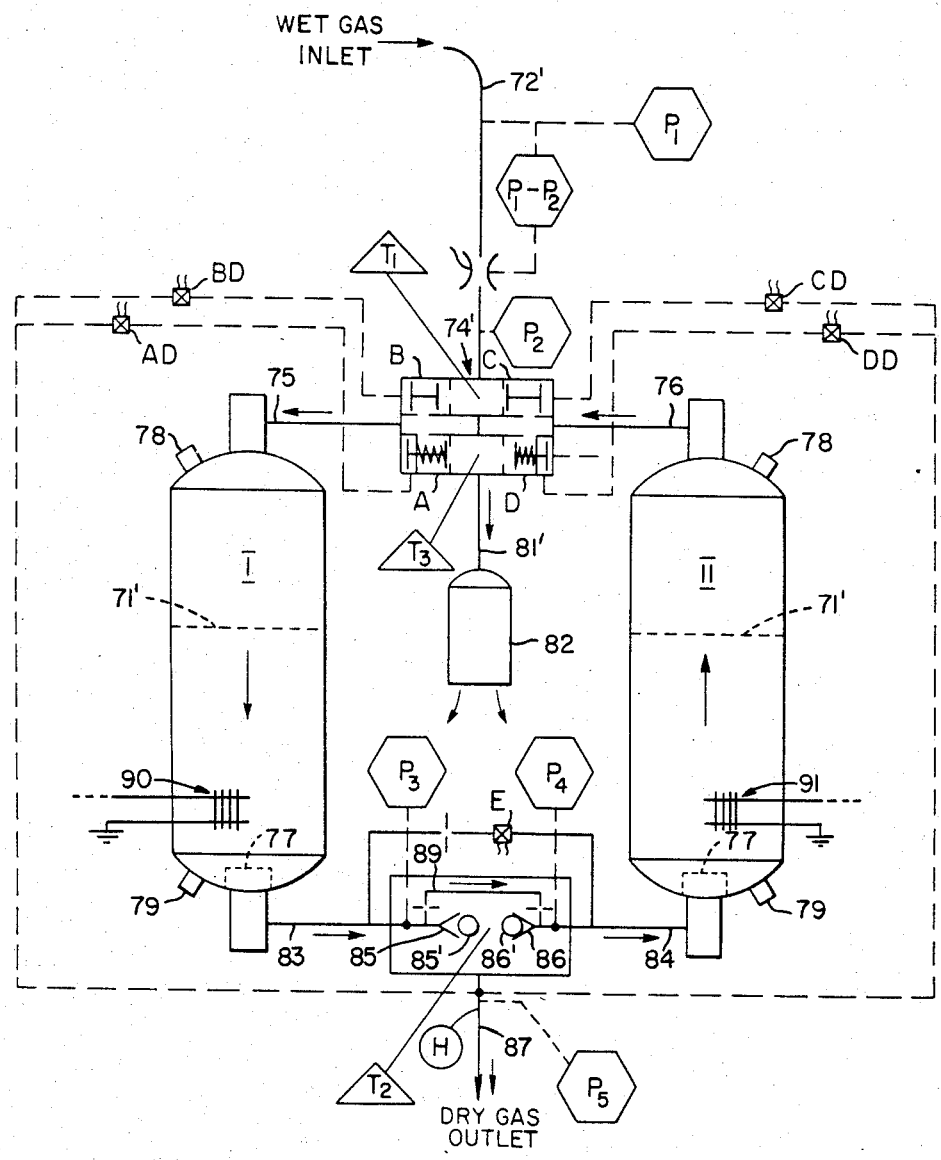
FIG. 6 is a schematic view of an electronic timer-controlled two-bed heat-regenerated desiccant dryer in accordance with the invention.
Figure 7:
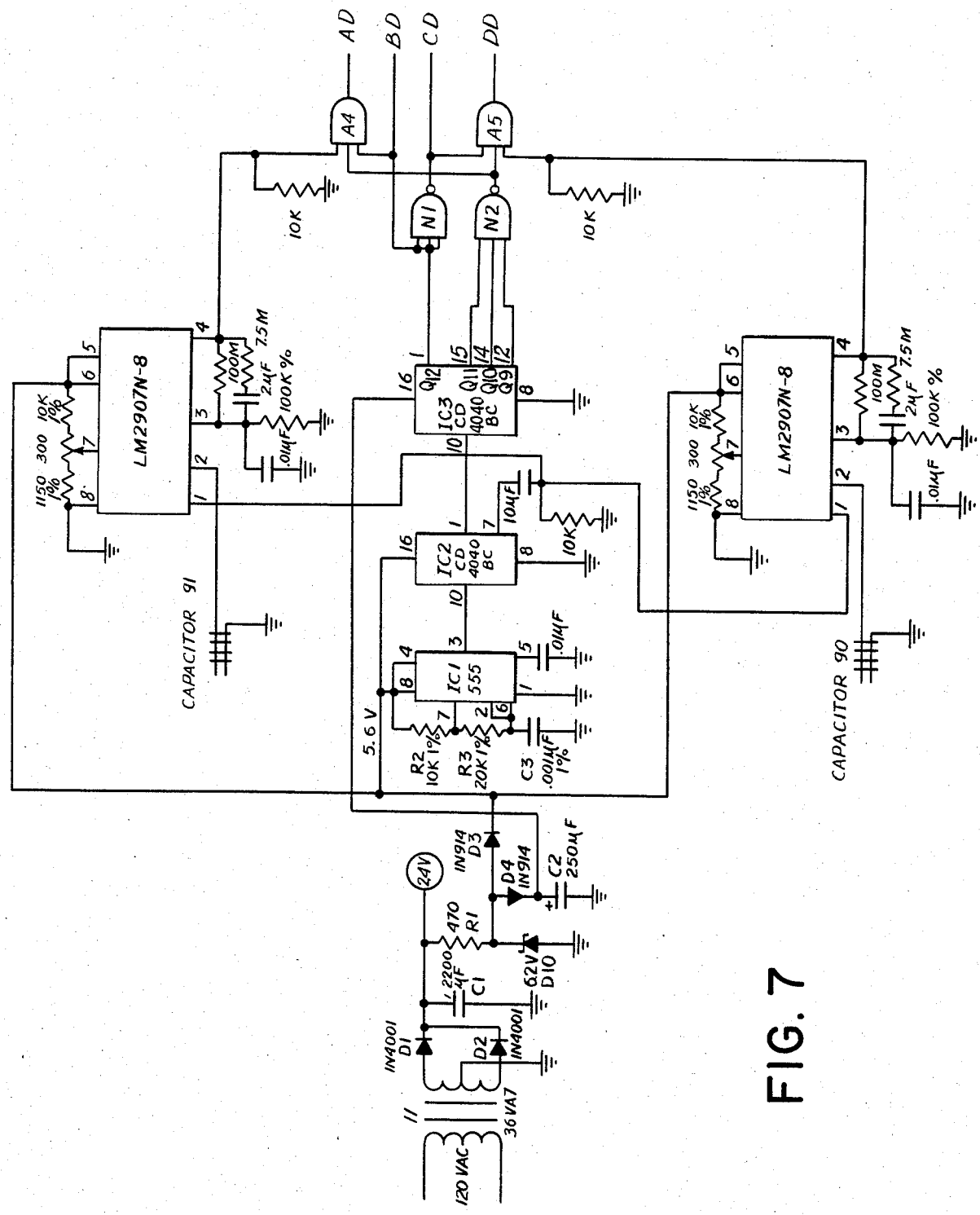
FIG. 7 is a detail view of the electronic sequence timer circuit of a dryer.
Figure 8:
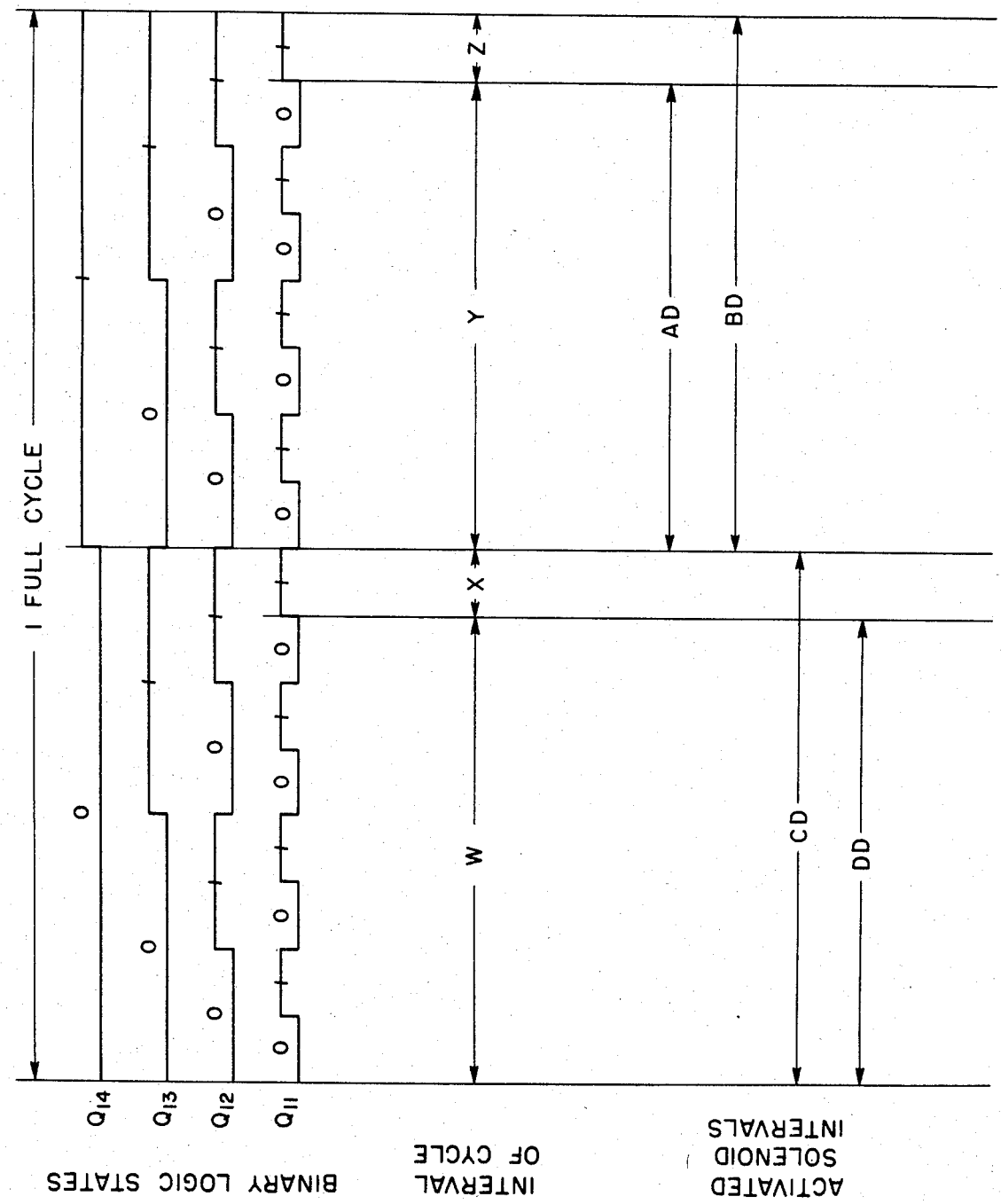
FIG. 8 is a timing digram showing the timing interval sequence of the timer circuit of FIG. 7.

The dryer of FIGS. 6 to 8 utilizes such an electronic timer and is composed of a pair of desiccant tanks I and II. These tanks are disposed vertically. Each tank contains a bed 71' of desiccant such as silica gel or activated alumina. Also provided in tanks I and II are desiccant fill and drain ports 78, 79 for draining and filling of desiccant in the tanks.

Only two lines are required connecting the two tanks at top and bottom, respectively, for introduction of influent gas containing moisture to be removed, and for delivery of dry effluent gas, freed from moisture after having passed through the dryer, with the necessary valves A,B,C,D for switching flow of influent and effluent gas to and from each tank.

The four valves A,B,C,D are pneumatically driven by solenoid operated pilot valves AD,BD, CD and DD, which are connected to and controlled by the electronic sequence timer whose circuitry is shown in FIG. 7. The timing intervals for solenoid valves AD,BD, CD and DD are shown in FIG. 8.

As seen in FIG. 7, 24 volt D.C. power is derived through a 36 volt center tapped transformer T1 and rectifiers D1 and D2, and filtered with a 2200 Mfd electrolytic capacitor C1.

The low voltage logic potential is maintained by supplying a 6.2V 0.4W Zener diode D10 through a power-dissipating 470Ω resistor R1 from the filtered 24 V.D.C. supply. While this Zener regulation adds the advantage of power supply noise isolation to the function of reducing the supply voltage, it might not be necessary if the initial filtered supply and solenoid operating voltage were in the operating range of the logic IC's (15 volts or less).

This low voltage is split into two supplies by diodes D3 and D4 so that the charge on 250 Mfd capacitor C2 can be used to maintain a small leakage current into the integrated circuit IC2 to retain memory of cycle position in the event of short term power failure. These two diodes are used to maintain the same supply voltage (Vcc) on all logic integrated circuits (approximately 6 volts).

The integrated circuit 555 timer IC1 is set to oscillate at 27.962 kHz for a 10 minute cycle by the proper selection of precision resistors R2 and R3 and capacitor C3 used in its oscillator circuit.

The 555 timer is a highly stable device for generating accurate time delays or oscillation with a normally-on and normally-off output timing from microseconds through hours, an adjustable duty cycle, and operational in both astable and monostable nodes. In the system shown, it is operated in the astable mode, in which the timer will trigger itself and free-run as a multivibrator. The external capacitor charges through R2+R3 and discharges through R3. Thus, the duty cycle may be set precisely by the ratio of these two resistors, and the resistors can be changed as required to achieve the desired ratio.

The capacitor charges and discharges between ⅓ Vcc and ⅔ Vcc. The charge and discharge times and frequency are independent of the supply voltage. The charge time is given by the equation:

$$t_1 = 0.693(R1+R3)C3$$

and the discharge time by the equation:

$$t_2 = 0.693(R3)C3$$

Thus, the total period is $T = t_1 + t_2 = 0.693(R2+2R3)C3$. Any desired time cycle can of course be selected, and IC1 set accordingly.

The output of the oscillator drives the first stage of a 14 bit I.C. binary counter IC2.

IC2 serves to reduce the frequency of the output of IC1. It provides two frequencies, one from pin 7 to drive pin 1 of the LM2907 and one from pin 1 to drive pin 10 of IC3.

IC3 is a CMOS twelve stage ripple-carry binary counter/divider identical to IC2 and consists of a pulse input shaping circuit, reset line driver circuitry, and twelve ripple-carry binary counter stages. Buffered outputs are externally available from stages 1 through 12. The counter is reset to its "all zeros" state by a high level on the reset inverter input line. This reset is not used in this application. Each counter stage is a static master-slave flip flop. The counter is advanced one count on the negative-going transition of each input pulse. With this integrated circuit, each bit is changed in stage between logic 0 and logic 1 when triggered by the negative going pulse (logic 1 to logic 0 of the preceding state). Each stage therefore reverses logic state at half the frequency of the preceding stage, keeping a 12 bit binary record of where the unit is in its cycle, as seen in FIG. 8. In the last portion of the timing cycle, all 12 bits are at logic state 1. The next negative swing of the oscillator drives all bits 2 to logic state 0, and the next cycle begins. The last four bits $Q_9$, $Q_{10}$, $Q_{11}$ and $Q_{12}$ of this counter contain the required information to divide the cycle into 16 even segments, and identify which portion the unit is in at all times.

These four bits are fed to a series of logic gates which determine the proper combination of logic states which satisfies the conditions under which each of the four outputs should be in their driving state.

The circuit includes two NAND gates N1, N2 and two AND gates A4,A5.

One input of AND gate A4 is connected to NAND gate N2, while another is connected directly to $Q_{12}$. The third input is connected to the capacitor output for the chamber controlled by valves A,B. The output of A4 is connected via the driving transistor (not shown) to solenoid valve AD. Only if all three inputs are 1, is solenoid A powered.

One input of AND gate A5 is connected to NAND gate N2, and one input is connected to NAND gate N1. The third input is connected to the capacitor output for the chamber controlled by valves C and D. The output of A5 is connected via the driving transistor (not shown) to solenoid valve DD.

$Q_{12}$ is connected via the driving transistor (not shown) to solenoid valve BD without the intervention of any gate.

It is powered when the $Q_{12}$ output is 1. NAND gate N1 is connected via the driving transistor (not shown) to solenoid valve CD, AND gate A5 as noted is similarly connected to solenoid valve DD.

Both of the NAND gates is of the three-input type, with the result that the only time there is 0 output is when all three inputs are 1. Since however all three inputs of N1 are connected to the same stage $Q_{12}$, this NAND gate is simply an inverter, and gives an output that drives the solenoid CD through its output transistor, only when there is 0 output from $Q_{12}$, but not otherwise.

NAND gate N2 has its three inputs connected respectively to stages $Q_9$, $Q_{10}$, and $Q_{11}$, and therefore gives an output of 1 unless all of $Q_9$, $Q_{10}$, and $Q_{11}$ are 1.

Solenoid valve DD is powered through its driving transistor by AND gate A5, which has three inputs, one from N1, one from N2, and one from the capacitance probe circuit. There is consequently an output of 1 from A5 to the solenoid valve DD driving transistor only if both N1 and N2 give outputs of 1, and if the probe senses moisture.

NAND gate N1 is a 1 during W and X, and at 0 during Y and Z. NAND gate N2 is at 1 during W and Y, and at 0 during X and Z. AND gate A4 is at 1 during Y, and at 0 during W,X and Z, and AND gate A5 is at 1 during W, and at 0 during X,Y and Z, assuming that the appropriate capacitance probe senses a sufficient moisture level to require purge.

Accordingly, the time intervals dictated by the timer and by the capacitors are as shown in FIG. 8. Solenoid valve CD is powered during intervals W and X, and solenoid valve DD during interval W. Solenoid valve BD is powered during intervals Y and Z, and solenoid valve AD during interval Y.

The power outputs of these gates switch the solenoid drivers or driving transistors $Q_1$, $Q_2$, $Q_3$, and $Q_4$, (not shown) on and off through current limiting resistors R4, R5, R6, and R7 (not shown). These transistors drive the solenoid valves AD,BD,CD, DD, shown in FIG. 6 and are protected from inductive fly-back by diodes D5, D6, D7, and D8 (not shown).

The intervals W+X and Y+Z correspond to the drying cycle times for the tanks I and II, respectively.

The intervals W and Y correspond to the regeneration stage for the tanks II and I, respectively, and the intervals X and Z correspond to the repressurization stage when regeneration is complete. The capacitors operate valves A and D and so control regeneration flow and halt chamber effluent flow when regeneration is complete, allowing repressurization, while the timer operates valves B and C and so changes influent from one chamber to the other.

The line 72' conducts the moist influent gas to the four-component inlet switching valve 74', including valves A,B,C,D. One of valves C,B directs the flow of influent gas to one of two inlet lines 75 and 76, one of lines 75,76 always leading the influent gas to the top of each tank I,II and the other of lines 75,76 according to valves A,D loading the purge flow of regeneration effluent gas to the exhaust via line 81' and muffler 82, venting to atmosphere.

Within each desiccant bed 71', the bottom is a capacitor 90, 91, connected to AND gates A4 and A5, as noted above. At the bottom of each tank is a desiccant support 77 made of a perforated metal cylinder, retaining the desiccant bed 71' in the tanks I and II. Outlet lines 83 and 84 from the bottom of tanks I and II, respectively, lead to the pair of ball check valves 85,86. Valve 74' is operated by the electronic sequence timer through its solenoid operated pilot valves, but valves 85, 86 are pressure operated. The ball in the effluent line from the on-stream tanks I and II is displaced on switching and start up of on-stream flow in lines 83,84, while the other one of the balls 84', 86' at such switching time moves against the seat, closing off the lines 83, 84 leading to the chamber undergoing regeneration at reduced pressure, and thus directing main effluent flow via the outlet line 87.

Disposed in each outlet lines 83 and 84 is a filter screen, which is movable, and is also made of sintered stainless wire mesh. This acts to retain any desiccant particles that might otherwise be carried out from the bed 71' past the desiccant support 77, to keep the outlet valves 85,86 and the remainder of the system clean of such particles.

From valves 85,86 extends the dry gas effluent delivery line 87, to deliver the dired effluent gas from the dryer to the system being supplied therewith. In the line 87 there can be placed an outlet pressure gauge $P_5$ and a humidity sensor II, but these are optional, and can be omitted.

A cross line 89 having a narrow passage bridges the outlet lines 83,84 bypassing valves 85,86 when either is closed, and providing purge flow to the line 83,84 leading to the off-stream tank. Line 89 due to its small diameter has a pressure-reducing function, inasmuch as downstream thereof pressure is reduced to approximately atmospheric when one of purge valves A,D is open, and it also meters the volume of purge flow bled off the effluent gas at valves 85,86 for regeneration of the spent tank. Purge exhaust valves A,D control purge flow via lines 75,76 according to signal from the electronic sequencer which opens and closes them at the proper time, via the appropriate solenoid actuated pilot valves. Solenoid valve E, on another restricted flow line, is operated during repressurization to speed this process on dryers with faster cycle times. It is optional, depending on dryer size and speed.

If the left-hand tank I is on the drying cycle, and the right-hand tank II on the regenerating cycle, then valves 74'B and D are open, 74'C and A closed, and the operation of the dryer proceeds as follows: wet gas influent at, for example, 100 psig, and a flow rate of 305 s.c.f.m., saturated at 80° F., enters through the inlet line 72', passes the valve 74'B (valve C being closed) and enters the top of the first tank I, and passes thence downwardly through the bed of desiccant 71' therein, for example, silica gel or activated alumina, to the bottom of the tank, and thence through supports 77 and line 83, valve 85 to the dry gas outlet line 87. Effluent gas is delivered there at 95 psig and 265 s.c.f.m., dewpoint minus 100° F. The ball 86' prevents entry of dry gas into line 84 except via line 89. This metered remainder of the dry gas effluent, 40 s.c.f.m., is bled off through the line 89, where its pressure is reduced to approximately atmospheric, and then passes through line 84 to the bottom of the second tank II, which is on the regeneration cycle. Purge flow passes upwardly through the desiccant bed 71', and emerges at the top into line 76, and thence passes through valve 74'D, to line 81' and muffler 82, where it is vented to the atmosphere.

This cycle continues until the regeneration is completed as sensed by the capacitor 91, whereupon the capacitor 91 gives signal and closes purge exhaust valve D by deactivating pilot valve DD. Accordingly, line 89 slowly repressurizes tank II. The system continues with tank I on the drying cycle until the fixed cycle time W+X has elapsed, whereupon the electronic sequence timer reverses valves 74'C,B, and the cycle begins again with the chambers reversed.

The time W+X (and Y+Z) that each bed will be on the drying cycle is greater by interval X (and Z) than the length of time W (and Y) required to regenerate the spent bed. When the regeneration time has elapsed, as sensed by capacitor 91 valve D (or as sensed by capacitor 90, valve A) is shut off, and the regenerated tank is then automatically and slowly repressurized via line 89. This repressurization may be accelerated by opening optional valve E.

When the fixed cycle time W+X has elapsed, the electronic sequence timer switches valves 74'C,B, so that wet gas influent entering through the inlet 72' passes through line 76 to the top of tank II, while check valve 86 shifts to open line 84, whereupon check valve 85 shifts to close line 83, so that dry gas effluent can now pass from the bottom of the tank II to the dry gas delivery line 87, while line 83 is closed, except to the flow of purge gas bypassing valve 85 via the cross-line 89, now reversed. Purge flow proceeds via line 83 to the bottom of tank I, which is on the regeneration cycle, and thence upwardly through the bed to the line 75 and thence through valve 74'A, line 81', and muffler 82, where it is vented to the atmosphere.

Usually, the drying cycle is carried out with gas at a superatmospheric pressure, of the order of 15 to 350 psig. The orifice in the cross-line 89 in combination with the purge exhaust valves A and D ensures that the regeneration cycle is carried out at a pressure considerably reduced from that at which the adsorption cycle is effected.

The dryer systems of the invention can be used with any type of sorbent adapted to adsorb moisture from gases. Activated carbon, alumina, silica gel, magnesia, various metal oxides, clays, fuller's earth, bone char, and Mobilbeads, and like moisture-adsorbing compounds can be used as the desiccant.

Molecular sieves also can be used, since in many cases these have moisture-removing properties. This class of materials includes zeolites, both naturally-occurring and synthetic, the pores in which may vary in diameter from the order of several angstrom units to from 12 to 15 A, or more. Chabasite and analeite are representative natural zeolites that can be used. Synthetic zeolites that can be used include those described in U.S. Pat. Nos. 2,442,191 and 2,306,610. All of these materials are well known as desiccants, and detailed descriptions thereof will be found in the literature.

The dryers described and shown in the drawings are all adapted for purge flow regeneration with the purge passing in counterflow to the wet gas influent. This, as is well known, is the most efficient way of utilizing a desiccant bed. As a wet gas passes through a desiccant bed in one direction, the moisture content of the desiccant progressively decreases, and normally the least amount of moisture will have been adsorbed at the outlet end of the bed. It is consequently only sound engineering practice to introduce the regenerating purge gas from the outlet end, so as to avoid driving moisture from the wetter part of the bed into the drier part of the bed, and thus lengthen the regeneration cycle time required. If the purge flow be introduced at the outlet end, then the moisture present there, although it may be in a small amount, will be removed by the purge flow and brought towards the wetter end of the bed. Thus, the bed is progressively regenerated from the outlet end, and all the moisture is carried for the least possible distance through the bed before it emerges at the inlet end.

Nonetheless, for some purposes, it may be desirable to run the purge flow in the same direction as the influent flow. In accordance with the invention, it is possible to carry the moisture content of the desiccant to a very high level, much higher than is normally feasible, because of the protecting action of the humidity sensing element, which makes it possible to cut off flow at a time more precisely gauged to moisture level than has heretofore been possible. Consequently, in many cases if the bed is brought nearly to the saturation point throughout, it will make little difference if the purge flow enters at the influent end or at the outlet end, and the invention contemplates both types of operation, although of course counterflow regeneration is preferred in most cases.

The drying apparatus illustrated in the drawings each employ one capacitor per tank. However, it is also possible to employ two, three or more of such capacitors per tank. This will ensure operation of the device despite failure of one or more capacitors in the group. The capacitors can be placed at different levels in the desiccant bed, so as to follow the passage of the moisture front progressively through the bed. As stated previously as the drying cycle continues, the moisture front gradually moves from the inlet end towards the outlet end of the bed. Therefore, the passage of the front will of course actuate a capacitor further from the outlet end sooner than a capacitor nearer the outlet end. Two capacitors spaced at a significant distance from each other will actuate at different times, and this fact can be used to actuate different stages of the cycle, such as regeneration and repressurization, at different times.

Thus, it is possible to employ one capacitor at a point spaced a considerable distance from the outlet end of the bed, say, halfway down the bed, to detect the front at time A of the cycle, and actuate the cutting off of the heaters in the bed being regenerated, for example so that these are cut off early enough to ensure cooling of the bed on the regenerating cycle before it is put on the drying cycle. A second intermediate capacitor can be used to actuate closing of the purge exhaust valves, and repressurize the regenerated bed. A third capacitor at the far end of the bed may actuate the switching of the cycle switches, and terminate the drying cycle. In this case, of course, no timer is needed, and the regeneration cycle time is determined not by a timer but by the capacitor.

The influent gas stream may on occasion be contaminated with gas and liquid substances other than the substance intended to be adsorbed, such as water which upon adsorption on the sorbent change the dielectric constant in a way different from the intended adsorband and "poison" the desiccant. Such contaminants may reduce the sorbent capacity to adsorb water, or may coadsorb with water, and change the response of the capacitor by displacing water, which has a high dielectric constant, and replacing it with a contaminant with a lower or higher dielectric constant. Any of these responses would result in a spurious indication of moisture content at a given level in the sorbent bed.

By placing two capacitors in each bed, one at the chosen control point, and a second farther from the influent end of the bed, the erroneous response can be corrected. The control capacitor would be exposed to the effects of any such contaminant before the second capacitor would be. By taking into account the effect of variations in bed position on capacitor output, in the absence of contaminant, the effect of such contaminant on capacitor response could be detected by comparing the output of the two capacitors, either continuously or intermittently, and designating a contaminated condition when the second capacitor gave a higher output than the control capacitor. The comparison would reveal whether the capacity of the sorbent at the control capacitor had been impaired by contaminant, or whether the dielectric constant had been changed by contaminant, and hence whether the control capacitor was in error.

The capacitor within the desiccant bed can be at any depth within the diameter of the bed, but the distance from the outlet is dependant on the gas velocity and temperature which influence the rate of travel and the contour of the moisture front in the bed. Other factors discussed previously are moisture content of the influent gas and the moisture content or level at which the capacitor is actuated.

The capacitors can be arranged to detect by way of moisture content of the sorbent any desired moisture level in the effluent gas, even very low dewpoints or relative humidities, although usually it is sufficient for it to detect a moisture content in the range above about $-30°$ C. dewpoint. The moisture level for the dry gas effluent from the desiccant bed is not normally below and about $-130°$ F. dewpoint at the outlet end of the bed.

Figure 1:
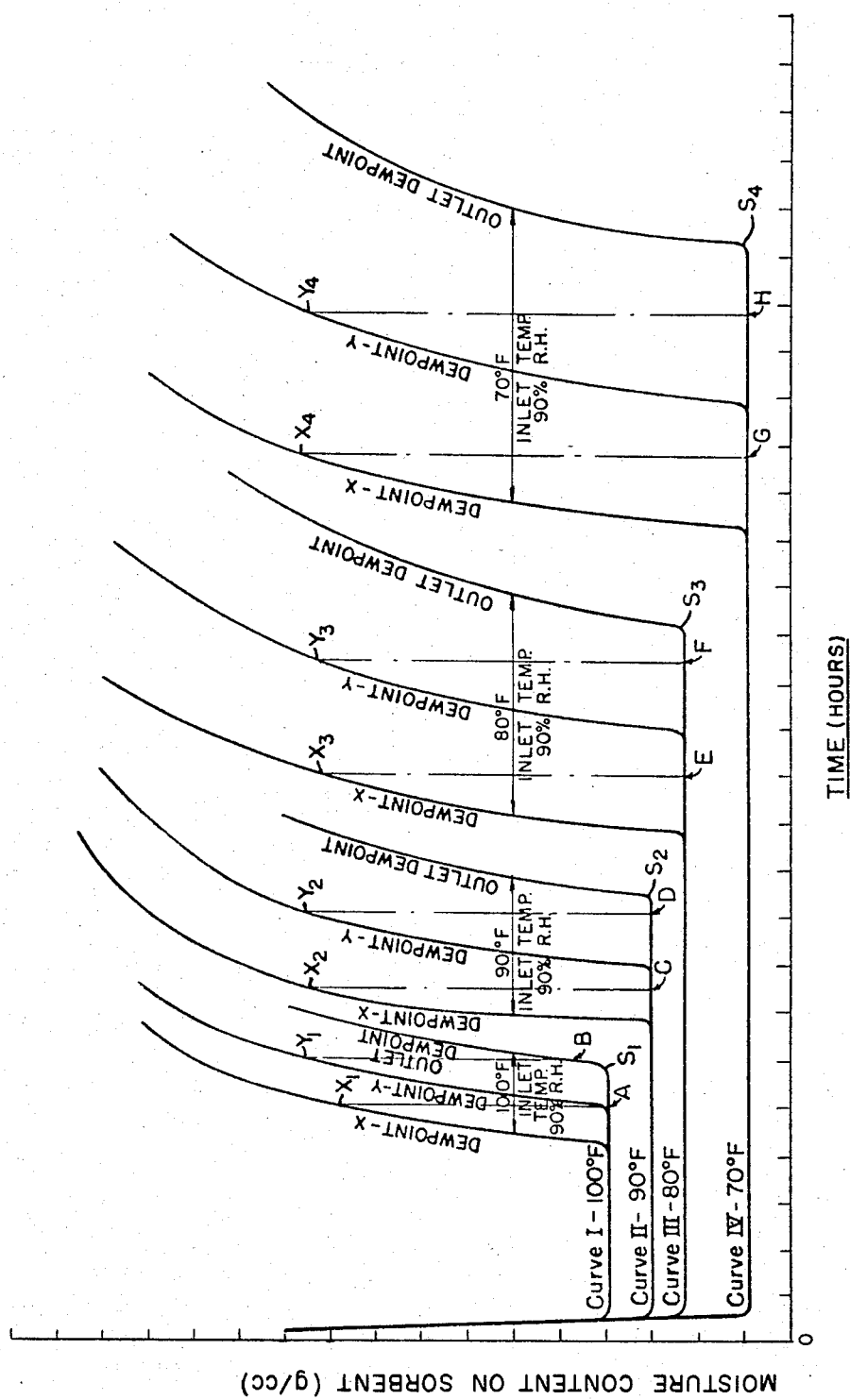

The precise location of the capacitors in the bed is determined by one of two factors, the length of time to regenerate the bed, and the prevention of effluent dewpoint breakthrough. Clearly, the capacitors must be located and adjusted so that the capacitors will sense a high moisture level in the sorbent bed before the effluent dewpoint becomes excessive, under most adverse conditions of influent flow rate, humidity and temperature. This may be done as shown in FIG. 1. However, the capacitors must be located so that the amount of water required to saturate a bed sufficiently to actuate the capacitors can be desorbed in the regeneration time cycle provided. Thus, in a dryer where the regeneration time increases disproportionately with the increased water content in the bed, such as a heaterless type, the capacitors will be moved closer to the inlet and the bed considered spent at a lower total moisture content in the bed than in a heated dryer.

As stated previously, taking the above factors into consideration, the proper positioning of the capacitors for detection of the moisture front at the proper time for terminating a drying cycle under any given adsorption conditions can be determined empirically, obtaining and graphing dewpoint-time or relative humidity-time data for the drying apparatus, as illustrated in FIG. 1 of U.S. Pat. No. 3,448,561.

Preliminary tests on the change in dielectric constant of desiccant with changes in the amount of water adsorbed onto the desiccant have been made using a test fixture consisting of two metal plates of 100.25 inch surface area spaced 0.75 inch. The space between the plates was filled with either dry or saturated samples of either alumina or silica gel desiccant. The values of capacitance measured were as follows:

|  | DRY | WET | WET/DRY RATIO |
| --- | --- | --- | --- |
| Alumina | 94.35 pF | 591 pF | 6.3 |
| Silica Gel | 97.0 pF | 331 pF | 3.4 |

A test to determine the effect of oil on the capacitance of desiccant was also made by measuring the capacitance of a sample of dry alumina in the fixture, removing the alumina and mixing it with an excess of oil, returning the alumina-oil mixture to the text fixture and measuring the capacitance again. The dry alumina gave a capacitance of 97.5 pF and the alumina-oil mixture gave a capacitance of 102.0 pF, indicating that any reasonable level of oil contamination should have a negligible effect on such a capacitor.

The following Examples in the opinion of the inventors represent a preferred method of operation of a dryer system in accordance with the invention:

EXAMPLE 1

A two bed heat-reactivatable dryer of the type shown in FIG. 3 having two desiccant beds 60 inches long and 12⅜ inches in diameter, containing 177 lbs of silica gel, was used to dry air at 80% relative humidity, 100° F. to 70° F., and 92 p.s.i.g. inlet pressure and 350 scfm flow. The superficial flow velocity of the air was 65.1 feet per minute at 100° F. Two capacitors X and Y, actuatable at about 3% relative humidity, corresponding to a sorbent moisture content of 2%, were placed in the bed, X at 30 inches and Y at 24 inches from the outlet end of the bed. The following are the data for four drying cycles carried out using this apparatus under these conditions, in each case terminating the drying cycle when capacitor Y was alarmed:

TABLE I

| Inlet temp. (°F.) | Time to alarm at sensors (hrs) | | Effluent dewpoint (°F.) at line pressure | | |
|---|---|---|---|---|---|
| | X | Y | Start of run | Time X alarmed | Time Y alarmed |
| 100 | 2 | 2.4 | −71 | −69 | −68 |
| 90 | 2.7 | 3.3 | −75 | −74 | −74 |
| 80 | 3.7 | 4.5 | −79 | −75 | −74 |
| 70 | 5.2 | 6.3 | −84 | −82 | −82 |

It is apparent from the data that the capacitors X and Y each alarmed at a time to terminate the drying cycle at a safe moisture level in the effluent gas. It is also clear from the different times of the cycle that the capacitors made it possible to adjust cycle length to match variation in moisture level of the influent air, and thus preserve desiccant life by cutting down the number of regenerations materially. In order to ensure delivery of effluent gas of the proper moisture level, had this dryer been on a timed cycle interval, it would have been necessary to set the cycle interval at less than 2.4 hours, say 2.2 hours to prevent breakthrough at 100° F., since if it had run beyond this, the moisture level of the effluent gas might have exceeded the requirements. The cycle time can be extended to as high as 6.2 hours, if air at 70° F. and accordingly less moisture is introduced. It is apparent that as the moisture content of the influent air is reduced further, cycle time will be extended accordingly. Much longer times are possible if flow rate or inlet temperature are reduced accordingly.

EXAMPLE 2

A two bed heaterless dryer of the type shown in FIG. 4 having two desiccant beds 53 inches long and 8 inches in diameter containing 85 lbs of alumina per bed was used to dry air at 50% relative humidity, 70° F. and 68 p.s.i.g. inlet pressure. The flow rate was 125 s.c.f.m., equal to a superficial flow velocity of 58 feet per minute. Eight capacitors A to H, spaced about 6 inches apart, as shown in Table II, sensing between 2½ and 16% adsorbed water were placed in the bed. These were used to detect the concentration gradient from the inlet to the outlet of the bed by measuring moisture content of the sorbent alumina at each point.

TABLE II

| Inches from inlet: | Capacitor |
|---|---|
| 2 | A |
| 9 | B |
| 15 | C |
| 22 | D |
| 28 | E |

TABLE II-continued

| Inches from inlet: | Capacitor |
|---|---|
| 34 | F |
| 41 | G |
| 48 | H |

Figure 2:
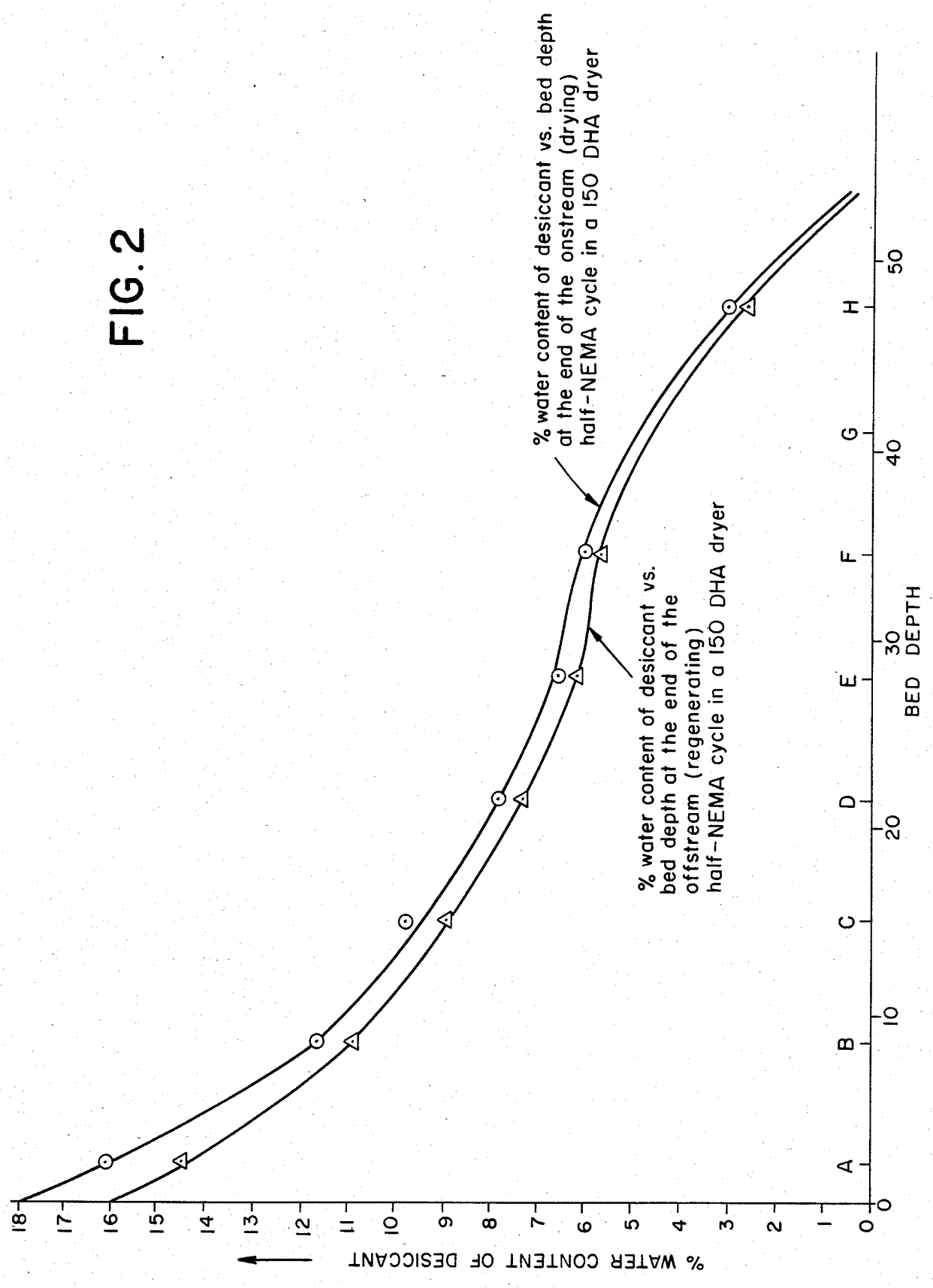
FIG. 2 is a gaph of sorbent bed moisture content determined as a function of capacitance against time, according to Example 2.

The moisture content of the sorbent bed was graphed against time, as shown in FIG. 2. The upper line corresponds to the absorbed moisture profile in bed at the end of the onstream half-cycle for the bed. The lower line corresponds to the adsorbed moisture profile at the end of the regeneration half-cycle. Adsorbed water content at the outlet end of the bed (53.5 in.) is calculated assuming equilibrium with outlet air. Thus the cycle could have been terminated at any point, as might be required to ensure delivery of effluent gas of the proper moisture level.

While the invention has been described with principal emphasis on a desiccant dryer and a process for drying gases, it will be apparent to those skilled in the art that this apparatus with a suitable choice of sorbent can be used for the separation of one or more gaseous components from a gaseous mixture. In such a case, the adsorbed component can also be removed from the sorbent by application of heat, and optionally, in addition, a reduction in pressure, during regeneration. Thus, the process can be used for the separation of hydrogen from petroleum hydrocarbon streams and other gas mixtures containing the same, for the separation of oxygen from nitrogen, for the separation of olefins from saturated hydrocarbons, and the like. Those skilled in the art are aware of sorbents which can be used for this purpose.

In may cases, sorbents useful for the removal of moisture from air can also be used, preferentially to adsorb one or more gas components from a mixture thereof, such as activated carbon, glass wool, absorbent cotton, metal oxides and clays such as attapulgite and bentonite, fuller's earth, bone char and natural and synthetic zeolites. The zeolites are particularly effective for the removal of nitrogen, hydrogen and olefins, such as ethylene or propylene, from a mixture with propane and higher paraffin hydrocarbons, or butene or higher olefins. The selectivity of a zeolite is dependent upon the pore size of the material. The available literature shows the selective adsorptivity of the available zeolites, so that the selection of a material for a particular purpose is rather simple and forms no part of the instant invention.

In some cases, the sorbent can be used to separate a plurality of materials in a single pass. Activated alumina, for example, will adsorb both moisture vapor and carbon dioxide, in contrast to Mobilbeads which will adsorb only water vapor in such a mixture.

The apparatus employed for this purpose will be the same as that described and shown in FIGS. 3 to 8, inclusive, and the process is also as described, suitably modified according to the proportions of the components to be separated, the operating pressure and temperature and the volume of available sorbent.

It will, however, be understood that the process is of particular application in the drying of gases, and that this is the preferred embodiment of the invention.

Having regard to the foregoing disclosure, the following is claimed as inventive and patentable embodiments thereof:

1. Apparatus having a sorbent bed for alternately adsorbing and thereby reducing the concentration of first gas in a mixture thereof with a second gas to below a limiting maximum concentration thereof in the second gas and then regenerating the sorbed bed by desorption of adsorbed first gas without application of heat, comprising, in combination, a vessel; a chamber therein for a bed of sorbent having a preferential adsorptivity for the first gas and that is regenerated by desorption of first gas without application of heat; a line for delivering influent gas at an inlet end of said bed; a line for delivering effluent gas from an outlet end of said bed; a capacitor positioned between the inlet and outlet ends of the bed and having two conductors of selected surface area spaced from each other a sufficient distance to define a space sized to accommodate a volume of sorbent as the dielectric whose change in first gas content, detected as a function of dielectric constant, causes a change in capacitance thereof; means for closing off the influent flow of gas after a predetermined first time interval; means responsive to the change in capacitance to give a first signal in response to a first predetermined capacitance indicating a first selected first gas content has been reached at the end of said time interval; means for depressurizing the sorbent bed and for introducing a purge gas to regenerate the sorbent in response to the first signal; and means for returning the sorbent bed to the adsorption mode after a second predetermined time interval whereby depressurization and purge is omitted under low loading conditions.

2. Apparatus in accordance with claim 1, wherein said capacitor is positioned approximately midway between the inlet and outlet ends of the bed, the apparatus further comprising means responsive to the change in capacitance to give a second signal when a second predetermined capacitance indicating a second selected first gas content is reached during any regeneration, said second selected first gas content being substantially lower than said first selected first gas content; and means for halting regeneration in response to the second signal prior to the expiration of the second time interval thereby conserving purge flow and energy used in regeneration of the bed.

3. Apparatus in accordance with claim 1 wherein said means responsive to the change in capacitance to give said first signal comprise means for generating a voltage in response to said capacitance and means for generating said first signal in response to said voltage reaching a predetermined first voltage.

4. Apparatus in accordance with claim 1 wherein said signalling means is operated electrically, and hysteresis is introduced into the signalling means to terminate regeneration at a slightly lower sensed capacitance.

5. Apparatus in accordance with claim 4 in which the signalling means comprises an electronic signal-conditioning circuit and said hystersis is introduced by a resistor whose value determines the difference between the two capacitance levels at which the output of the circuit goes to a high or low state.

6. Apparatus in accordance with claim 1 comprising a pair of vessels, each having chambers therein for a bed of sorbent, and each having lines for delivery of influent gas and for delivery of effluent gas.

7. Apparatus in accordance with claim 6 comprising means for diverting a portion of effluent gas from one vessel to the other vessel for purge flow desorption of sorbed first gas from the bed.

8. Apparatus in accordance with claim 1 wherein the capacitor comprises an open array of at least three flat parallel sheet conductors interleaved with alternate sheets connected together in conducting relation and arranged in the bed with the planes of the sheet conductors substantially in line with the flow of gas through the bed.

9. A process for reducing the concentration of first gas in mixture thereof with a second gas to below a limiting maximum concentration thereof in the second gas, which comprises passing the mixture through a bed of a sorbent having a preferential affinity for the first gas; adsorbing first gas thereon to form a gaseous effluent having a concentration thereof below the maximum, and forming a concentration gradient of first gas in the bed progressively decreasing from one end to the other end as the adsorption continues and an increasing concentration of first gas in the second gas defining a concentration front progressively advancing in the bed from one end to the other end as sorbent capacity thereof decreases; closing off the influent flow of gas after a predetermined time interval being calculated to assure that effluent having greater than the maximum first gas content would not leave the bed under maximum contemplated loading conditions; sensing the advance of the first gas front in the bed by determining the change in the first gas content of the sorbent as a function of the capacitance of a capacitor in which the sorbent is the dielectric at a point between the inlet and outlet ends of the bed, conditionally depressurizing the sorbent bed and introducing a purge gas to regenerate said sorbent without application of heat at the end of said time interval only when said capacitance is at least equal to a first predetermined capacitance indicating a first selected first gas content in said sorbent, and returning the sorbent bed to the adsorption mode after a second predetermined time interval, whereby depressurization and purge is omitted under low loading conditions.

10. The process of claim 9 wherein the sorbent being the dielectric of said capacitor is at a point approximately midway between the inlet and outlet ends of the bed, and wherein during any regeneration the process further comprises the step of halting said regeneration in response to said capacitance becoming equal to a second predetermined capacitance indicating a second selected first gas content in said sorbent, thereby conserving purge flow and energy used in regenerating the beds.

11. The process of claim 9, further comprising the steps of generating a voltage responsive to said capacitance and comparing said voltage to a first predetermined voltage to indicate whether said capacitance is equal to said first predetermined capacitance.

12. Apparatus for reducing the concentration of first gas in a mixture thereof with a second gas to below a limiting maximum concentration thereof in the second gas, comprising, in combination, a vessel; a chamber therein for a bed of sorbent having a preferential affinity for the first gas; a line for delivering influent gas at an inlet end of said bed; a line for delivering effluent gas from an outlet end of said bed; a capacitor comprising an open array of at least three flat parallel sheet conductors interleaved with alternate sheets connected together in conducting relation and arranged in the bed with the planes of the sheet substantially in-line with the flow in a manner to directly intercept a substantial portion of the gas flow through the bed, the sheet conductors being coated with an electrically insulating layer so that the capacitor is isolated from the conductivity of said sorbent, the sheets being of selected surface area and spaced from each other a sufficient distance to define a space sized to accommodate a volume of sorbent as the dielectric change in first gas content, detected as a function of dielectric constant, causes a change in capacitance thereof; means responsive to the change in capacitance to give a signal when a selected capacitance indicating a selected first gas content is reached or exceeded; and means for regenerating the sorbent bed in response to the signal.

13. Apparatus in accordance with claim 12 wherein said means responsive to the change in capacitance to give said signal comprise means for generating a voltage in response to said capacitance and means for generating said signal in response to said voltage reaching a predetermined voltage.

* * * * *